(12) United States Patent
Clark et al.

(10) Patent No.: US 9,550,994 B2
(45) Date of Patent: Jan. 24, 2017

(54) RNAI-MEDIATED INHIBITION OF FRIZZLED RELATED PROTEIN-1 FOR TREATMENT OF GLAUCOMA

(71) Applicant: Arrowhead Research Corporation, Pasadena, CA (US)

(72) Inventors: Abbot F. Clark, Arlington, TX (US); Wan-Heng Wang, Fort Worth, TX (US); Loretta Graves McNatt, Hurst, TX (US); Jon E Chatterton, Aliso Viejo, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 14/692,402

(22) Filed: Apr. 21, 2015

(65) Prior Publication Data
US 2015/0307882 A1 Oct. 29, 2015

Related U.S. Application Data

(62) Division of application No. 13/429,913, filed on Mar. 26, 2012, now Pat. No. 9,040,494, which is a division of application No. 13/084,944, filed on Apr. 12, 2011, now Pat. No. 8,173,617, which is a division of application No. 11/373,376, filed on Mar. 10, 2006, now Pat. No. 7,947,660.

(60) Provisional application No. 60/688,633, filed on Jun. 8, 2005, provisional application No. 60/660,556, filed on Mar. 11, 2005.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 9/00* | (2006.01) |
| *A61K 31/7088* | (2006.01) |
| *A61K 38/00* | (2006.01) |

(52) U.S. Cl.
CPC ........... *C12N 15/113* (2013.01); *A61K 9/0048* (2013.01); *A61K 31/7088* (2013.01); *A61K 38/00* (2013.01); *A61K 48/00* (2013.01); *C12N 2310/111* (2013.01); *C12N 2310/14* (2013.01)

(58) Field of Classification Search
CPC . A61K 38/00; C12N 15/113; C12N 2310/111; C12N 2310/14
See application file for complete search history.

(56) References Cited

U.S. PATENT DOCUMENTS

| | | |
|---|---|---|
| 6,326,193 B1 | 12/2001 | Liu et al. |
| 6,506,559 B1 | 1/2003 | Fire et al. |
| 7,592,324 B2 | 9/2009 | Shepard et al. |
| 7,622,454 B2 | 11/2009 | Shepard et al. |
| 2002/0049177 A1 | 4/2002 | Clark et al. |
| 2002/0086356 A1 | 7/2002 | Tuschl et al. |
| 2002/0162126 A1 | 10/2002 | Beach et al. |
| 2003/0027783 A1 | 2/2003 | Zernicka-Goetz et al. |
| 2003/0143732 A1 | 7/2003 | Fosnaugh et al. |
| 2003/0153524 A1 | 8/2003 | Hinton et al. |
| 2004/0029275 A1 | 2/2004 | Brown et al. |
| 2004/0038921 A1 | 2/2004 | Kreutzer et al. |
| 2004/0053411 A1 | 3/2004 | Cullen et al. |
| 2004/0072769 A1* | 4/2004 | Yin ..................... C12Q 1/6837 514/44 A |
| 2004/0115195 A1 | 6/2004 | Bodine |
| 2004/0147475 A1 | 7/2004 | Li et al. |
| 2004/0175732 A1 | 9/2004 | Rana |
| 2004/0186159 A1 | 9/2004 | Hellberg et al. |
| 2004/0203145 A1 | 10/2004 | Zamore et al. |
| 2004/0259247 A1 | 12/2004 | Tuschl et al. |
| 2005/0164907 A1 | 7/2005 | Clark et al. |
| 2005/0203043 A1 | 9/2005 | Fedorov et al. |
| 2005/0223427 A1 | 10/2005 | Leake et al. |
| 2005/0246794 A1 | 11/2005 | Khvorova et al. |
| 2005/0255487 A1 | 11/2005 | Khvorova et al. |
| 2006/0172961 A1 | 8/2006 | Clark et al. |
| 2006/0172963 A1 | 8/2006 | Shepard et al. |
| 2006/0216732 A1 | 9/2006 | Clark et al. |
| 2006/0223773 A1 | 10/2006 | Clark et al. |
| 2007/0031844 A1 | 2/2007 | Khvorova et al. |

FOREIGN PATENT DOCUMENTS

| | | |
|---|---|---|
| CA | 2359180 | 7/2001 |
| WO | 00044895 | 8/2000 |
| WO | 0136646 A1 | 5/2001 |
| WO | 0164949 A3 | 9/2001 |
| WO | 0168836 | 9/2001 |
| WO | 0168836 A3 | 3/2002 |
| WO | 0244321 A2 | 6/2002 |
| WO | 02044321 A3 | 10/2003 |
| WO | 03092475 A2 | 11/2003 |
| WO | 03092705 A1 | 11/2003 |
| WO | 2004022782 A2 | 3/2004 |
| WO | 2004076639 A2 | 9/2004 |
| WO | 2005019453 A2 | 3/2005 |
| WO | 2005079815 A2 | 9/2005 |

OTHER PUBLICATIONS

US 2002/0114785 A1, 08/2002, Li et al. (withdrawn)
Bass; "The short answer"; News and Views; Nature; vol. 411; pp. 428-429; (May 24, 2001).
Elbashir et al.; "Analysis of gene function in somatic mammalian cells using small interfering RNAs"; Methods; vol. 26; pp. 199-213 (2002).

(Continued)

*Primary Examiner* — Amy Bowman
(74) *Attorney, Agent, or Firm* — Kirk Ekena

(57) ABSTRACT

RNA interference is provided for inhibition of Frizzled Related Protein-1 mRNA expression, in particular, for treating patients having glaucoma or at risk of developing glaucoma.

8 Claims, 1 Drawing Sheet

(56) References Cited

OTHER PUBLICATIONS

Morgan et al; "A more efficient and specific strategy in the ablation of mRNA in Xenpous laevis using mixtures of antisense oligos"; Nucleic Acids Research; vol. 21; No. 19; pp. 4615-4620 (1993).
Clark, A.F., et al.; "Increased Expression of sFRP-1 Glaucomatous Trabecular Meshwork and Presence of a Functional WNT Signaling Pathway that Regulates IOP"; Database Biosis Biosciences Information Service, Philadelphia, PA; Database Accession No. PREV200300165428; ARVO Annual Meeting Abs Search and Program Planner. 2002.
Wang, Feng-Sheng, et al.; "Secreted Frizzled-Related Protein 1 Modulates Glucocorticoid Attenuation of Osteogenic Activities and Bone Mass"; Endocrinology; pp. 2415-2423; vol. 146; No. 5; 2005.
Ambros; "The functions of animal microRNAs"; Nature; pp. 350-355; vol. 431; 2004.
Arias; "Frizzeld at the Butting Edge of the Synapse"; Science; pp. 1284-1285; vol. 31; 2005.
Bartel; "MicroRNAs: Genomics, Biogenesis, Mechanism, and Function"; Cell; pp. 281-297; vol. 116; 2004.
Bafico, et al.; "Interaction of Frizzled Related Protein (FRP) with Wnt Ligands and the Frizzled Receptor Suggests Alternative Mechanisms for FRP Inhibition of Wnt Signaling"; The Journal of Biological Chemistry; pp. 16180-16187; vol. 274; No. 23: 1999.
Dorsett, et al.; "SIRNAs: Applications in Functional Genomics and Potential as Therapeutics"; Nature; pp. 318-329; vol. 3; 2004.
Echeverri, et al.; "siRNA Design: It's All in the Algorithm"; Ambion TechNotes.
Elbashir, et al.; "Duplexes of 21-nucleotide RNAs Mediate RNA Interference in Cultured Mammalian Cells"; Letters to Nature; pp. 494-498; vol. 411; 2001.
Elbashir, et al.; "Functional Anatomy of siRNAs for Mediating Efficient RNAi in Drosophila melanogaster embryo lysate"; The EMBO Journal; pp. 6877-6888; vol. 20; No. 23; 2001.
Elbashir, et al.; "RNA interference is mediated by 21- and 22-nucleotide RNAs"; Genes & Development; pp. 188-200; vol. 15; 2001.
Hannon, et al.; "Unlocking the potential of the human genome with RNA Interference"; Nature; pp. 371-378; vol. 431; 2004.
Harborth, et al.; "Sequence, Chemical, and Structural Variation of Small Interfering RNAs and Short Hairpin RNAs and the Effect on Mammalian Gene Silencing"; Antisense and Nucleic Acid Drug Development; pp. 83-105; vol. 13; 2003.
He, et al.; "MicroRNAs: Small RNAs With a Big Role in Gene Regulation"; Reviews; pp. 522-531; vol. 5; 2004.
Jackson, et al.; "Expression Profiling Reveals Off-Target Gene Regulation by RNAI"; Nature Biotechnology; pp. 535-638; vol. 21; No. 6; 2003.
Kawasaki, et al.; "Induction of DNA methylation and gene silencing by short interfering RNAs in human cells"; Nature; pp. 211-217; vol. 431; 2004.
Kim, et al.; "Synthetic dsRNA Dicer substrates enhance RNAi potency and efficacy"; Nature Biotechnology; pp. 222-226; vol. 23; 2005.
Lim, et al.; "Vertebrate MicroRNA Genes"; Science; pp. 1540; vol. 299; 2003.
Liu, et al.; "Argonaute2 is the Catalytic Engine of Mammalian RNAi"; Science; pp. 1437-1441; vol. 305; 2004.
Morris, et al.; "Small Interfering RNA-Induced Transcriptional Gene Silencing in Human Cells"; Science; pp. 1289-1292; vol. 305; 2004.
Novina, et al.; "The RNAi revolution"; Nature; pp. 161-164; vol. 430; 2004.
Paddison, et al.; "Short hairpin RNAs (shRNAs) induce sequence-secific silencing in mammalian cells"; Genes & Development; pp. 948-958; vol. 16; 2002.
Pang, et al.; "Preliminary characterization of a transformed cell strain derived from human trabecular meshwork"; current Eye Research; pp. 51-63; vol. 13; No. 1; 1994.
Shepard, et al.; "Importance of quantitative PCR primer location for short interfering RNA efficacy determination"; Analytical Biochemistry; pp. 287-288; vol. 344; 2005.
Soutschek, et al.; "Therapeutic silencing of an endogenous gene by systemic administration of modified SiRNAs"; Nature; pp. 173-178; vol. 432; 2004.
Zhou, et al.; "Inhibitionof HIV-1 Fusion With Small Interfering RNAs Targeting the Chemokine Coreceptor CXCR4"; Gene Therapy; pp. 1703-1712; vol. 11; 2004.
Couzin, Jennifer; Science; vol. 306; 1124-1125; 2004.
"PsiRNA System a simple and innovative tool to create Shore Hairpin siRNAs" Small Interfering RNAs (siRNA): psiRNA System, pp. 1-3, http://www.invivogen.com/siRNA/psiRNA_system.htm, printed Nov. 3, 2004.
"SiRNA Design Guidelines", Ambion Technical Bulletin #506, pp. 1-8, 2004, Ambion, Inc., http://www.invivogen.com/siRNA/siRNA_overview.htm, printed Nov. 3, 2004.

* cited by examiner

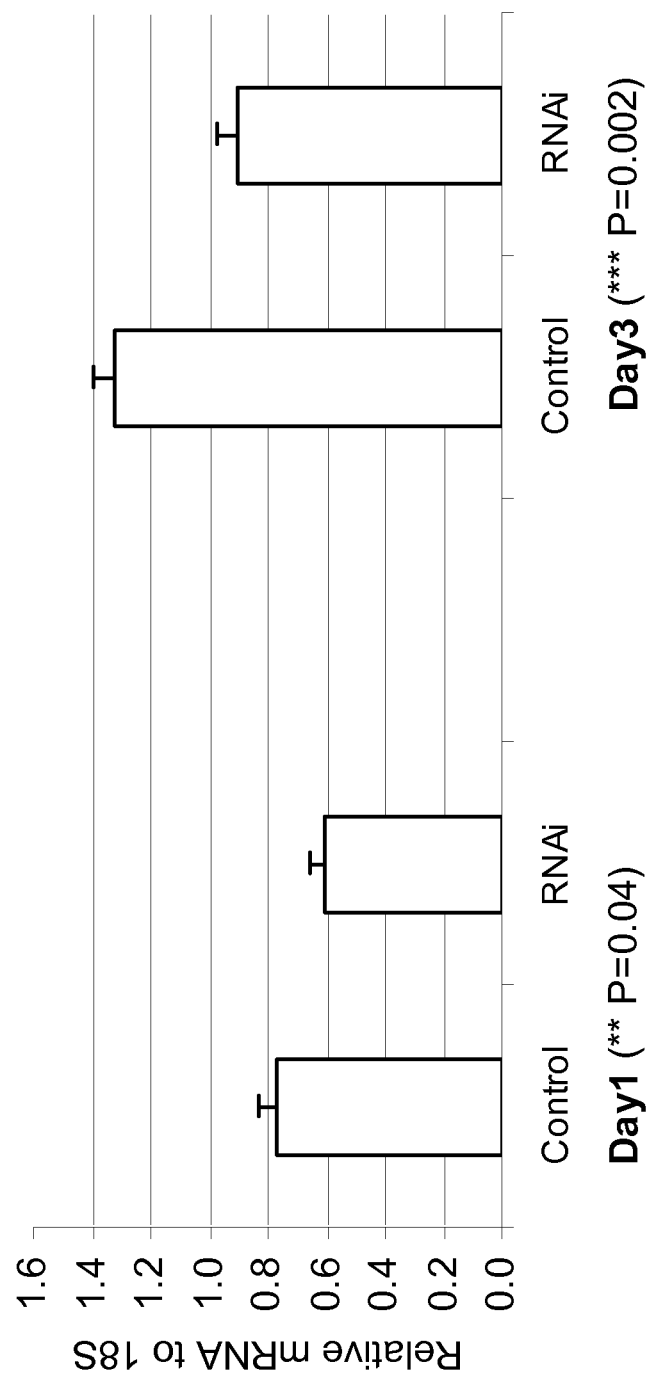

RNAI-MEDIATED INHIBITION OF FRIZZLED RELATED PROTEIN-1 FOR TREATMENT OF GLAUCOMA

This application is divisional of application Ser. No. 13/429,913, filed Mar. 26, 2012 and issued as U.S. Pat. No. 9,040,494, which is a divisional of application Ser. No. 13/084,944, filed Apr. 12, 2011 and issued as U.S. Pat. No. 8,173,617, which is a divisional al application Ser. No. 11/373,376, filed Mar. 10, 2006 and issued as U.S. Pat. No. 7,947,660, which claims the benefit of U.S. Provisional Application No. 60/660,556 filed Mar. 11, 2005, and 60/688,633, filed Jun. 8, 2005, each of which is incorporated herein by reference.

FIELD OF THE INVENTION

The present invention relates to the field of interfering RNA compositions for treatment of glaucoma by inhibition of expression of Frizzled Related Protein-1 (FRP-1).

BACKGROUND OF THE INVENTION

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the optic nerve head (ONH). One of the main risk factors for the development of glaucoma is the presence of ocular hypertension (elevated intraocular pressure, IOP). An adequate intraocular pressure is needed to maintain the shape of the eye and to provide a pressure gradient to allow for the flow of aqueous humor to the avascular cornea and lens. IOP levels may also be involved in the pathogenesis of normal tension glaucoma (NTG), as evidenced by patients benefiting from IOP lowering medications. Once adjustments for central corneal thickness are made to IOP readings in NTG patients, many of these patients may be found to be ocular hypertensive.

The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous ONH. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

Primary glaucomas result from disturbances in the flow of intraocular fluid that has an anatomical or physiological basis. Secondary glaucomas occur as a result of injury or trauma to the eye or a preexisting disease. Primary open angle glaucoma (POAG), also known as chronic or simple glaucoma, represents ninety percent of all primary glaucomas. POAG is characterized by the degeneration of the trabecular meshwork, resulting in abnormally high resistance to fluid drainage from the eye. A consequence of such resistance is an increase in the IOP that is required to drive the fluid normally produced by the eye across the increased resistance.

Current anti-glaucoma therapies include lowering IOP by the use of suppressants of aqueous humor formation or agents that enhance uveoscleral outflow, laser trabeculoplasty, or trabeculectomy, which is a filtration surgery to improve drainage. Pharmaceutical anti-glaucoma approaches have exhibited various undesirable side effects. For example, miotics such as pilocarpine can cause blurring of vision and other negative visual side effects. Systemically administered carbonic anhydrase inhibitors (CAIs) can also cause nausea, dyspepsia, fatigue, and metabolic acidosis. Further, certain beta-blockers have increasingly become associated with serious pulmonary side effects attributable to their effects on beta-2 receptors in pulmonary tissue. Sympathomimetics cause tachycardia, arrhythmia and hypertension. Such negative side effects may lead to decreased patient compliance or to termination of therapy. In addition, the efficacy of current IOP lowering therapies is relatively short-lived requiring repeated dosing during each day and, in some cases, the efficacy decreases with time.

In view of the importance of glaucoma, and the inadequacies of prior methods of treatment, it would be desirable to have an improved method of treatment.

SUMMARY OF THE INVENTION

The present invention overcomes these and other drawbacks of the prior art by providing highly potent and efficacious treatment, prevention or intervention of glaucoma and pre-glaucoma related conditions. In one aspect, the methods of the invention include treating a subject having glaucoma or at risk of developing glaucoma by administering interfering RNAs that silence expression of FRP-1 mRNA, thus interfering with the Wnt signaling pathway and preventing a cascade of events related to glaucoma and pre-glaucoma cellular activity.

The term "glaucoma" as used herein, includes ocular pre-glaucoma conditions, such as hypertension, and ocular glaucoma conditions, and includes those cellular changes resulting from the expression of FRP-1-mRNA that lead directly or indirectly to glaucoma and glaucoma-related conditions. The interfering RNA provided herein provides for such silencing while avoiding toxic side effects due to nonspecific agents.

The present invention is directed to interfering RNAs that target FRP-1 mRNA and thereby interfere with FRP-1 mRNA expression. The interfering RNAs of the invention are useful for treating patients with glaucoma or at risk for developing glaucoma.

An embodiment of the invention is a method of attenuating expression of Frizzled Related Protein-1 mRNA of a subject, the method comprising administering to the subject a composition comprising an effective amount of interfering RNA having a length of 19 to 49 nucleotides and a pharmaceutically acceptable carrier. The expression of Frizzled Related Protein-1 mRNA is attenuated thereby.

Another embodiment of the invention is a method of treating glaucoma in a subject in need thereof is an embodiment of the invention. The method comprises administering to an eye of the subject a composition comprising an effective amount of interfering RNA having a length of 19 to 49 nucleotides, and a pharmaceutically acceptable carrier. The glaucoma is treated thereby. The subject is a human and the human has glaucoma in one embodiment of the invention. In another embodiment, the subject is a human and the human is at risk of developing glaucoma.

For the above cited embodiments, the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:2, SEQ ID NO:8-SEQ ID NO:190, and SEQ ID NO:192.

In further embodiments of the above-cited methods, the composition further comprises a second interfering RNA having a length of 19 to 49 nucleotides and comprising a region of at least 13 contiguous nucleotides having at least 90% sequence complementarity to, or at least 90% sequence identity with, the penultimate 13 nucleotides of the 3' end of a second mRNA corresponding to any one of SEQ ID NO:2, SEQ ID NO:8-SEQ ID NO:190, and SEQ ID NO:192.

In yet another embodiment of the invention, a method of attenuating expression of Frizzled Related Protein-1 mRNA of a subject comprises administering to the subject a composition comprising an effective amount of interfering RNA having a length of 19 to 49 nucleotides and a pharmaceutically acceptable carrier and the interfering RNA comprises a sense nucleotide strand, an antisense nucleotide strand, and a region of at least near-perfect contiguous complementarity of at least 19 nucleotides where the antisense strand hybridizes under physiological conditions to a portion of mRNA corresponding to SEQ ID NO:1 or SEQ ID NO:191, and has a region of at least near-perfect contiguous complementarity of at least 19 nucleotides with the hybridizing portion of mRNA corresponding to SEQ ID NO:1 or SEQ ID NO:191, respectively. The expression of Frizzled Related Protein-1 mRNA is attenuated thereby.

A method of treating glaucoma in a subject in need thereof is an embodiment of the invention, the method comprising administering to an eye of the subject a composition comprising an effective amount of interfering RNA having a length of 19 to 49 nucleotides, and a pharmaceutically acceptable carrier, the interfering RNA comprising a sense nucleotide strand, an antisense nucleotide strand, and a region of at least near-perfect contiguous complementarity of at least 19 nucleotides; wherein the antisense strand hybridizes under physiological conditions to a portion of mRNA corresponding to SEQ ID NO:1 or SEQ ID NO:191 and has a region of at least near-perfect contiguous complementarity of at least 19 nucleotides with the hybridizing portion of mRNA corresponding to SEQ ID NO:1 or SEQ ID NO:191, respectively. The glaucoma is treated thereby.

For the above-cited methods, the antisense strand of the interfering RNA is designed to target an mRNA corresponding to SEQ ID NO:1 comprising nucleotide 509, 521, 524, 767, 818, 843, 850, 872, 881, 900, 959, 968, 971, 983, 986, 989, 1001, 1016, 1019, 1022, 1031, 1034, 1052, 1088, 1121, 1127, 1207, 1360, 1445, 1450, 1478, 1487, 1524, 1535, 1562, 1579, 1613, 1661, 1667, 1724, 1730, 1753, 1757, 1763, 1771, 1794, 1800, 1813, 1887, 1893, 1916, 2001, 2006, 2106, 2117, 2135, 2142, 2152, 2200, 2203, 2206, 2241, 2263, 2276, 2279, 2389, 2410, 2430, 2464, 2468, 2482, 2502, 2506, 2572, 2645, 2666, 2681, 2697, 2715, 2734, 2760, 2770, 2783, 2797, 2807, 2844, 2917, 2937, 2961, 3005, 3010, 3080, 3130, 3150, 3156, 3179, 3185, 3196, 3244, 3281, 3345, 3350, 3365, 3372, 3403, 3410, 3424, 3428, 3450, 3453, 3460, 3596, 3668, 3672, 3746, 3762, 3776, 3786, 3789, 3826, 3835, 3844, 3847, 3867, 3912, 3924, 3958, 3976, 3981, 4012, 4022, 4071, 4089, 4154, 4157, 4208, 4369, 4375, 4441, 966, 408, 409, 463, 754, 862, 863, 864, 868, 874, 909, 913, 915, 956, 1118, 1135, 1634, 1637, 1640, 1737, 1867, 1868, 2100, 2259, 2260, 2483, 2598, 2673, 2675, 2779, 2985, 2986, 2987, 2988, 3055, 3062, 3161, 3217, 3355, 3623, 3648, 3665, 3817, 4153, or 4252. In a further embodiment, the antisense strand of the interfering RNA is designed to target an mRNA corresponding to SEQ ID NO:191 comprising nucleotide 3352.

A second interfering RNA having a length of 19 to 49 nucleotides could also be administered to the subject; the second interfering RNA comprising a sense nucleotide strand, an antisense nucleotide strand, and a region of at least near-perfect complementarity of at least 19 nucleotides wherein the antisense strand of the second interfering RNA hybridizes under physiological conditions to a second portion of mRNA corresponding to SEQ ID NO:1 or SEQ ID NO:191, and the antisense strand has a region of at least near-perfect contiguous complementarity of at least 19 nucleotides with the second hybridizing portion of mRNA corresponding to SEQ ID NO:1 or SEQ ID NO:191, respectively.

A method of attenuating expression of Frizzled Related Protein-1 mRNA of a subject, comprising administering to the subject a composition comprising an effective amount of a single-stranded interfering RNA having a length of 19 to 49 nucleotides, and a pharmaceutically acceptable carrier, where the single-stranded interfering RNA hybridizes under physiological conditions to a portion of mRNA corresponding to SEQ ID NO:1 or SEQ ID NO:191 comprising the nucleotides identified above is a further embodiment of the invention.

The invention includes as a further embodiment a composition comprising an interfering RNA having a length of 19 to 49 nucleotides, and comprising a nucleotide sequence corresponding to any one of SEQ ID NO:2, SEQ ID NO:8-SEQ ID NO:190, and SEQ ID NO:192, or a complement thereof; and a pharmaceutically acceptable carrier.

Use of any of the embodiments as described herein in the preparation of a medicament for attenuating expression of FRP-1 mRNA as set forth herein is also an embodiment of the present invention.

BRIEF DESCRIPTION OF THE DRAWING

The drawing shows the effect of an interfering RNA on the level of endogenous FRP1 mRNA in COS7 cells as measured by QPCR. Significant inhibition of FRP1 mRNA was observed at day 1 (22%, P=0.04) and day 3 (32%, P=0.002) after transfection compared to controls as described in Example 1.

DETAILED DESCRIPTION OF THE INVENTION

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodi-ester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of Frizzled Related Protein-1 (FRP-1) mRNA, thus interfering with the Wnt signaling pathway and preventing a cascade of events related to glaucoma and pre-glaucoma cellular activity. According to the present invention, interfering RNAs provided exogenously or expressed endogenously are particularly effective at silencing Frizzled Related Protein-1 (FRP-1) mRNA in ocular tissue(s).

Frizzled Related Proteins (FRP) are a family of secreted proteins that antagonize the Wnt signaling pathway by binding extracelluar Wnt and preventing it from interacting with membrane-bound frizzled protein receptor or by forming a nonfunctional complex with the frizzled receptor (Bafico, et al. *J. Biol. Chem.*, 274(23):16180-16187 (1999)), thereby preventing a cascade of events related to differential adhesion of one cell to another as well as to an extracellular matrix.

The present inventors, together with others, as set forth by U.S. Published Patent Application No. 2004/0186159, application Ser. No. 10/488,496, to Hellberg, et al. (hereby incorporated by reference herein in its entirety), have determined that frizzled related protein (FRP) is differentially expressed in a number of glaucomatous trabecular meshwork cell lines. Perfusion of FRP-1 through perfused human ocular anterior segments maintained in culture resulted in a decrease in flow rate and a corresponding decrease in β-catenin protein levels in the ciliary body and the trabecular meshwork (TM). The decreased flow rate in the cultured anterior segments models an increase in resistance to outflow (increase in intraocular pressure) in intact eye.

Further, the present inventors, together with others, have shown that the expression of FRP-1 is upregulated in glaucomatous trabecular meshwork tissues and cells (U.S. Published Patent Application No. 2002/0049177, application Ser. No. 09/796,008 to Clark et al., entitled "Diagnostics and Therapeutics for Glaucoma" filed Feb. 28, 2001, incorporated by reference in its entirety).

These results show that there is an active Wnt signaling pathway in the trabecular meshwork and ciliary body and suggest that this pathway is responsible at least in part for maintaining outflow through the TM and thereby controlling IOP.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for FRP-1. The mRNA sequence is identical to the DNA sense strand sequence with the "T" bases replaced with "U" bases.

Therefore, the mRNA sequence of FRP-1 is known from SEQ ID NO:1, and the mRNA sequence of an equivalent of FRP-1 is known from SEQ ID NO:191.

Frizzled Related Protein (FRP-1) mRNA:

The GenBank database provides the DNA sequence for FRP-1 as accession no. AF056087, provided in the "Sequence Listing" as SEQ ID NO:1. SEQ ID NO:1 provides the sense strand sequence of DNA that corresponds to the mRNA encoding FRP-1 (with the exception of "T" bases for "U" bases). The coding sequence for FRP-1 is from nucleotides 303-1244.

Equivalents of the above cited FRP-1 mRNA sequence are alternative splice forms, allelic forms, isozymes, or a cognate thereof. A cognate is a Frizzled Related Protein-1 mRNA from another mammalian species that is homologous to SEQ ID NO:1 (i.e., an ortholog). FRP-1 nucleic acid sequences related to SEQ ID NO:1 include those having GenBank accession numbers NM_003012 (cited infra), BC036503, AF001900, BC004466, AF017987, and BT019677.

The GenBank database provides a further DNA sequence for FRP-1 as accession no. NM_003012, provided in the "Sequence Listing" as SEQ ID NO:191, and considered an equivalent to SEQ ID NO:1. SEQ ID NO:191 provides the sense strand sequence of DNA that corresponds to the mRNA encoding FRP-1 (with the exception of "T" bases for "U" bases). The coding sequence for secreted FRP-1 is from nucleotides 303-1247.

Attenuating Expression of an mRNA:

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting FRP-1 mRNA is administered. In other embodiments, two or more interfering RNAs targeting FRP-1 mRNA are administered.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of FRP-1 may also be determined in vitro by examining FRP-1 level, β-catenin levels or outflow rate in perfused anterior segments of human eyes as set forth in U.S. published patent application 2004/0186159 previously incorporated by reference herein. Briefly, ocular anterior segments are perfused with Dulbecco's modified Eagle's medium (DMEM) at a constant pressure of 11 mm Hg. The outflow rate of each eye is measured by weighing its reservoir at specified periods. After a stabilization period, the eyes are perfused with either a vehicle control, a scrambled siRNA sequence control, or an siRNA as described herein for attenuating FRP-1, and the outflow rates of the eyes monitored for 2-5 days. Aqueous humor outflow rate is measured by weighing its reservoir at specific periods. An increase in outflow as compared to the control values indicates that the siRNA is effective at attenuating FRP-1.

Inhibition of FRP-1 is also inferred in a human or mammal by observing an improvement in a glaucoma symptom such as improvement in intraocular pressure, improvement in visual field loss, or improvement in optic nerve head changes, for example.

Interfering RNA:

In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to an FRP-1 target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNAs.

An embodiment of a 19-nucleotide DNA target sequence for FRP-1 mRNA is present at nucleotides 509 to 527 of SEQ ID NO:1:

```
                                         SEQ ID NO: 2
         5'-CGTGGGCTACAAGAAGATG-3'.
```

An siRNA of the invention for targeting a corresponding mRNA sequence of SEQ ID NO:2 and having 21-nucleotide strands and a 2-nucleotide 3' overhang is:

```
                                         SEQ ID NO: 3
         5'-CGUGGGCUACAAGAAGAUGNN-3'

SEQ ID NO: 4
         3'-NNGCACCCGAUGUUCUUCUAC-5'.
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:2 and having 21-nucleotide strands and a 3'UU overhang on each strand is:

```
                                         SEQ ID NO: 5
          5'-CGUGGGCUACAAGAAGAUGUU-3'

SEQ ID NO: 6
          3'-UUGCACCCGAUGUUCUUCUAC-5'.
```

The interfering RNA may also have a 5' overhang of nucleotides or it may have blunt ends. An siRNA of the invention for targeting a corresponding mRNA sequence of SEQ ID NO:2 and having 19-nucleotide strands and blunt ends is:

```
                                   SEQ ID NO: 193
        5'-CGUGGGCUACAAGAAGAUG-3'

SEQ ID NO: 194
        3'-GCACCCGAUGUUCUUCUAC-5'.
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:2 and having a 19 bp double-stranded stem region and a 3'UU overhang is:

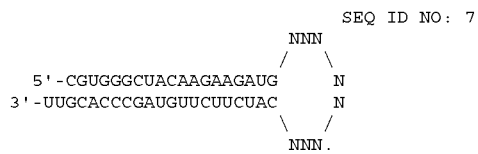

```
                                         SEQ ID NO: 7
                       NNN
                      /   \
      5'-CGUGGGCUACAAGAAGAUG   N
      3'-UUGCACCCGAUGUUCUUCUAC  N
                      \   /
                       NNN.
```

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:2) identified in the FRP-1 DNA sequence (SEQ ID NO:1) by 6 nucleotides yields a 25-nucleotide DNA target sequence present at nucleotides 509 to 533 of SEQ ID NO:1:

```
                                         SEQ ID NO: 195
        5'-CGTGGGCTACAAGAAGATGGTGCTG-3'.
```

A dicer-substrate 27-mer duplex of the invention for targeting a corresponding mRNA sequence of SEQ ID NO:195 is:

```
                                         SEQ ID NO: 196
        5'-CGUGGGCUACAAGAAGAUGGUGCUG-3'

SEQ ID NO: 197
        3'-UUGCACCCGAUGUUCUUCUACCACGAC-5'.
```

The two nucleotides at the 3' end of the sense strand (i.e., the UG nucleotides of SEQ ID NO:196) may be deoxynucleotides (i.e., TG) for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of FRP1 DNA target sequences of SEQ ID NO:1 and SEQ ID NO:191 from which siRNAs of the present invention are designed in a manner as set forth above. FRP1 encodes Frizzled Related Protein-1, as noted above.

TABLE 1

FRP1 Target Sequences for siRNAs

| FRP1 Target Sequence | # of Starting Nucleotide with reference to SEQ ID NO: 1 | SEQ ID NO: |
|---|---|---|
| CGTGGGCTACAAGAAGATG | 509 | 2 |
| GAAGATGGTGCTGCCCAAC | 521 | 8 |
| GATGGTGCTGCCCAACCTG | 524 | 9 |
| GTGTGACAAGTTCCCGGAG | 767 | 10 |
| TGCCACCGAAGCCTCCAAG | 818 | 11 |
| GGCACAACGGTGTGTCCTC | 843 | 12 |
| CGGTGTGTCCTCCCTGTGA | 850 | 13 |
| CGAGTTGAAATCTGAGGCC | 872 | 14 |
| ATCTGAGGCCATCATTGAA | 881 | 15 |
| CATCTCTGTGCCAGCGAGT | 900 | 16 |
| TGGCGACAAGAAGATTGTC | 959 | 17 |
| GAAGATTGTCCCCAAGAAG | 968 | 18 |
| GATTGTCCCCAAGAAGAAG | 971 | 19 |
| GAAGAAGAAGCCCCTGAAG | 983 | 20 |
| GAAGAAGCCCCTGAAGTTG | 986 | 21 |
| GAAGCCCCTGAAGTTGGGG | 989 | 22 |
| GTTGGGGCCCATCAAGAAG | 1001 | 23 |
| GAAGAAGGACCTGAAGAAG | 1016 | 24 |
| GAAGGACCTGAAGAAGCTT | 1019 | 25 |
| GGACCTGAAGAAGCTTGTG | 1022 | 26 |
| GAAGCTTGTGCTGTACCTG | 1031 | 27 |
| GCTTGTGCTGTACCTGAAG | 1034 | 28 |
| GAATGGGGCTGACTGTCCC | 1052 | 29 |
| CCTCAGCCACCACTTCCTC | 1088 | 30 |
| GGTGAAGAGCCAGTACTTG | 1121 | 31 |
| GAGCCAGTACTTGCTGACG | 1127 | 32 |
| ACCATGAGTGCCCCACCTT | 1207 | 33 |
| TCCAGTCGGCTTGTTCTTG | 1360 | 34 |
| AGCAAGGGCCATTTAGATT | 1445 | 35 |
| GGGCCATTTAGATTAGGAA | 1450 | 36 |
| GATCCGCAATGTGGAGCAG | 1478 | 37 |
| TGTGGAGCAGCAGCCACTG | 1487 | 38 |

TABLE 1-continued

FRP1 Target Sequences for siRNAs

| FRP1 Target Sequence | | SEQ ID NO: |
|---|---|---|
| ACCATTTCCAACAGCAACA | 1524 | 39 |
| CAGCAACACAGCCACTAAA | 1535 | 40 |
| AGGGGGATTGGGCGGAAAG | 1562 | 41 |
| AGTGAGAGCCAGCAGCAAA | 1579 | 42 |
| CTTGTTGGTGTGGATCTAT | 1613 | 43 |
| TTCTAATGATTGGCAAGTC | 1661 | 44 |
| TGATTGGCAAGTCACGTTG | 1667 | 45 |
| ATGGAAACAGACTCATACC | 1724 | 46 |
| ACAGACTCATACCACACTT | 1730 | 47 |
| TTAAGGTCAAGCCCAGAAA | 1753 | 48 |
| GGTCAAGCCCAGAAAGTGA | 1757 | 49 |
| GCCCAGAAAGTGATAAGTG | 1763 | 50 |
| AGTGATAAGTGCAGGGAGG | 1771 | 51 |
| GTGCAAGTCCATTATCTAA | 1794 | 52 |
| GTCCATTATCTAATAGTGA | 1800 | 53 |
| TAGTGACAGCAAAGGGACC | 1813 | 54 |
| TCTGAATCAGCCAGTCTCA | 1887 | 55 |
| TCAGCCAGTCTCAGATGCC | 1893 | 56 |
| AGTTTCGGTTCCTATGAGC | 1916 | 57 |
| AGGAAACCACAGTGAGCCT | 2001 | 58 |
| ACCACAGTGAGCCTGAGAG | 2006 | 59 |
| CAGTCCAGCAAATTGCTAG | 2106 | 60 |
| ATTGCTAGTCAGGGTGAAT | 2117 | 61 |
| TTGTGAAATTGGGTGAAGA | 2135 | 62 |
| ATTGGGTGAAGAGCTTAGG | 2142 | 63 |
| GAGCTTAGGATTCTAATCT | 2152 | 64 |
| GAACAATGACAAACACCCA | 2200 | 65 |
| CAATGACAAACACCCACTT | 2203 | 66 |
| TGACAAACACCCACTTATT | 2206 | 67 |
| CAGTCTACATTGAGCATTT | 2241 | 68 |
| AGGTGTGCTAGAACAAGGT | 2263 | 69 |
| CAAGGTCTCCTGATCCGTC | 2276 | 70 |
| GGTCTCCTGATCCGTCCGA | 2279 | 71 |
| GAGTCCGTGGTTGCCCTAG | 2389 | 72 |
| CCTAACACCCCTAGCAAA | 2410 | 73 |
| CTCACAGAGCTTTCCGTTT | 2430 | 74 |
| AGAAACATTTCCTTTGAAC | 2464 | 75 |
| ACATTTCCTTTGAACTTGA | 2468 | 76 |
| CTTGATTGCCTATGGATCA | 2482 | 77 |
| AGAAATTCAGAACAGCCTG | 2502 | 78 |
| ATTCAGAACAGCCTGCCTG | 2506 | 79 |
| AGTTGACATGGGTGGGGTG | 2572 | 80 |
| GTACCCTGAGATACTTCCC | 2645 | 81 |
| AGCCCTTATGTTTAATCAG | 2666 | 82 |
| TCAGCGATGTATAThAGCC | 2681 | 83 |
| GCCAGTTCACTTAGACAAC | 2697 | 84 |
| CTTTACCCTTCTTGTCCAA | 2715 | 85 |
| TGTACAGGAAGTAGTTCTA | 2734 | 86 |
| TGCATATTAATTTCTTCCC | 2760 | 87 |
| TTTCTTCCCCCAAAGCCGG | 2770 | 88 |
| AGCCGGATTCTTAATTCTC | 2783 | 89 |
| TTCTCTGCAACACTTTGAG | 2797 | 90 |
| CACTTTGAGGACATTTATG | 2807 | 91 |
| TGCTTATACCCAGTGAGGA | 2844 | 92 |
| AGGATGGTAGATTCTGTTA | 2917 | 93 |
| CTCTTGAAGACTCCAGTAT | 2937 | 94 |
| TCAGCATGCCCGCCTAGTT | 2961 | 95 |
| ATTAACCTCTCACAGTTAG | 3005 | 96 |
| CCTCTCACAGTTAGTGATC | 3010 | 97 |
| AGTGCTGGGGACCTTAAGT | 3080 | 98 |
| TGTGTATATATATTAGCTA | 3130 | 99 |
| TTAGAAATATTCTACTTCT | 3150 | 100 |
| ATATTCTACTTCTCTGTTG | 3156 | 101 |
| ACTGAAAATTCAGAGCAAGT | 3179 | 102 |
| ATTCAGAGCAAGTTCCTGA | 3185 | 103 |
| GTTCCTGAGTGCGTGGATC | 3196 | 104 |
| GAGTTCAGTGCTCATACGT | 3244 | 105 |
| AGTGCCTCATGCAACCGGG | 3281 | 106 |
| CATAAGTAGTTACCACAGA | 3345 | 107 |
| GTAGTTACCACAGAATACG | 3350 | 108 |
| TACGGAAGAGCAGGTGACT | 3365 | 109 |
| GAGCAGGTGACTGTGCTGT | 3372 | 110 |
| ATGGGAATTCTCAGGTAGG | 3403 | 111 |
| TTCTCAGGTAGGAAGCAAC | 3410 | 112 |
| GCAACAGCTTCAGAAAGAG | 3424 | 113 |
| CAGCTTCAGAAAGAGCTCA | 3428 | 114 |

TABLE 1-continued

FRP1 Target Sequences for siRNAs

| FRP1 Target Sequence | | SEQ ID NO: |
|---|---|---|
| TAAATTGGAAATGTGJATC | 3450 | 115 |
| ATTGGAAATGTGAATCGCA | 3453 | 116 |
| ATGTGAATCGCAGCTGTGG | 3460 | 117 |
| GGGAGGCTCTCTGTAGGCA | 3596 | 118 |
| CCAATGTGCAGACTGATTG | 3668 | 119 |
| TGTGCAGACTGATTGGCCT | 3672 | 120 |
| TTATCGCTAGGGCCJAGGT | 3746 | 121 |
| GGTGGGATTTGTAAAGCTT | 3762 | 122 |
| AGCTTTACAATAATCATTC | 3776 | 123 |
| TAATCATTCTGGATAGAGT | 3786 | 124 |
| TCATTCTGGATAGAGTCCT | 3789 | 125 |
| CTCAGTTAAATCTTTGAAG | 3826 | 126 |
| ATCTTTGAAGAATATTTGT | 3835 | 127 |
| GAATATTTGTAGTTATCTT | 3844 | 128 |
| TATTTGTAGTTATCTTAGA | 3847 | 129 |
| GATAGCATGGGAGGTGAGG | 3867 | 130 |
| TATCCTGTGTAACACTTGG | 3912 | 131 |
| CACTTGGCTCTTGGTACCT | 3924 | 132 |
| GTTCTCCCCAGGGTAGAAT | 3958 | 133 |
| TTCAATCAGAGCTCCAGTT | 3976 | 134 |
| TCAGAGCTCCAGTTTGCAT | 3981 | 135 |
| ATTACAGTAATCCCATTTC | 4012 | 136 |
| TCCCATTTCCCAAACCTAA | 4022 | 137 |
| CTGGTTGCTGTGTCATAAC | 4071 | 138 |
| CTTCATAGATGCAGGAGGC | 4089 | 139 |
| TAACATACTGGCCGTTCTG | 4154 | 140 |
| CATACTGGCCGTTCTGACC | 4157 | 141 |
| ATTCCCGTTTCCTCTAGTT | 4208 | 142 |
| TAGTAATTCCCGTACGTGT | 4369 | 143 |
| TTCCCGTACGTGTTCATTT | 4375 | 144 |
| TCACTCAATTAATCAATGA | 4441 | 145 |
| AAGAAGATTGTCCCCAAGAAG (SEQ ID NO: 18 with added 5' AA) | 966 | 146 |
| GTGAGCTTCCAGTCGGACA | 408 | 147 |
| TGAGCTTCCAGTCGGACAT | 409 | 148 |
| CACCTCAGTGCGTGGACAT | 463 | 149 |
| CCGAGATGCTTAAGTGTGA | 754 | 150 |
| CCTGTGACAACGAGTTGAA | 862 | 151 |
| CTGTGACAACGAGTTGAAA | 863 | 152 |
| TGTGACAACGAGTTGAAAT | 864 | 153 |
| ACAACGAGTTGAAATCTGA | 868 | 154 |
| AGTTGAAATCTGAGGCCAT | 874 | 155 |
| GCCAGCGAGTTTGCACTGA | 909 | 156 |
| GCGAGTTTGCACTGAGGAT | 913 | 157 |
| GAGTTTGCACTGAGGATGA | 915 | 158 |
| AAATGGCGACAAGAAGATT | 956 | 159 |
| CAAGGTGAAGAGCCAGTAC | 1118 | 160 |
| ACTTGCTGACGGCCATCCA | 1135 | 161 |
| GCTGATCTATGCCTTTCAA | 1634 | 162 |
| GATCTATGCCTTTCAACTA | 1637 | 163 |
| CTATGCCTTTCAACTAGAA | 1640 | 164 |
| CATACCACACTTACAATTA | 1737 | 165 |
| TCCGTGTGATTGTCTTTGA | 1867 | 166 |
| CCGTGTGATTGTCTTTGAA | 1868 | 167 |
| TTAGAACAGTCCAGCAAAT | 2100 | 168 |
| TGAAAGGTGTGCTAGAACA | 2259 | 169 |
| GAAAGGTGTGCTAGAACAA | 2260 | 170 |
| TTGATTGCCTATGGATCAA | 2483 | 171 |
| CCAGCGAGAGAGTTTCAAA | 2598 | 172 |
| ATGTTTAATCAGCGATGTA | 2673 | 173 |
| GTTTAATCAGCGATGTATA | 2675 | 174 |
| CCAAAGCCGGATTCTTAAT | 2779 | 175 |
| CCGGAGAGTTATCCTGATA | 2985 | 176 |
| CGGAGAGTTATCCTGATAA | 2986 | 177 |
| GGAGAGTTATCCTGATAAA | 2987 | 178 |
| GAGAGTTATCCTGATAAAT | 2988 | 179 |
| GGTTCTCTCTGACCTTTCA | 3055 | 180 |
| TCTGACCTTTCATCGTAAA | 3062 | 181 |
| CTACTTCTCTGTTGTCAAA | 3161 | 182 |
| GGTCTTAGTTCTGGTTGAT | 3217 | 183 |
| TACCACAGAATACGGAAGA | 3355 | 184 |
| CACTATCACGAGCCTTTGT | 3623 | 185 |
| CCACAAAGTATCTAACAAA | 3648 | 186 |
| AAACCAATGTGCAGACTGA | 3665 | 187 |
| TTGGCAGAACTCAGTTAAA | 3817 | 188 |

TABLE 1-continued

FRP1 Target Sequences for siRNAs

| FRP1 Target Sequence | | SEQ ID NO: |
|---|---|---|
| ATAACATACTGGCCGTTCT | 4153 | 189 |
| ATCCTAAGTCTCTTACAAA | 4252 | 190 |
| # of Starting Nucleotide with reference to SEQ ID NO: 191 | | |
| CATTAGTAGTTACCACAGA | 3352 | 192 |

As cited in the examples above, one of skill in the art is able to use the target sequence information provided in Table 1 to design interfering RNAs having a length shorter or longer than the sequences provided in Table 1 by referring to the sequence position in SEQ ID NO:1 or SEQ ID NO:191 and adding or deleting nucleotides complementary or near complementary to SEQ ID NO:1 or SEQ ID NO:191, respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical" to at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) J. Mol. Biol. 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

The target sequence in the mRNAs corresponding to SEQ ID NO:1 or SEQ ID NO:191 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1 or SEQ ID NO:191. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization Under Physiological Conditions:

In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m$° C.=$81.5+16.6(\log_{10}[Na+])+0.41$ (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-Stranded Interfering RNA:

As cited above, interfering RNAs ultimately function as single strands. Single-stranded (ss) interfering RNA has been found to effect mRNA silencing, albeit less efficiently than double-stranded RNA. Therefore, embodiments of the present invention also provide for administration of a ss interfering RNA that hybridizes under physiological conditions to a portion of SEQ ID NO:1 or SEQ ID NO:191 and has a region of at least near-perfect contiguous complementarity of at least 19 nucleotides with the hybridizing portion of SEQ ID NO:1 or SEQ ID NO:191, respectively. The ss interfering RNA has a length of 19 to 49 nucleotides as for the ds interfering RNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin Interfering RNA:

A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of Administration:

Interfering RNA may be delivered directly to the eye by ocular tissue administration such as periocular, conjunctival, subtenon, intracameral, intravitreal, intraocular, subretinal, subconjunctival, retrobulbar, intracanalicular, or suprachoroidal administration; by injection, by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal. Systemic or parenteral administration is contemplated including but not limited to intravenous, subcutaneous, transdermal, and oral delivery.

Subject:

A subject in need of treatment for glaucoma or at risk for developing glaucoma is a human or other mammal having glaucoma or at risk of developing a glaucoma-related condition, such as hypertension, associated with undesired or inappropriate expression or activity of FRP-1 as cited herein. Ocular structures associated with such disorders may include the eye, retina, choroid, lens, cornea, trabecular meshwork, iris, optic nerve, optic nerve head, sclera, aqueous chamber, vitreous chamber, ciliary body, or posterior segment, for example. A subject may also be an ocular cell, cell culture, organ or an ex vivo organ or tissue.

Formulations and Dosage:

Pharmaceutical formulations comprise interfering RNAs, or salts thereof, of the invention up to 99% by weight mixed with a physiologically acceptable ophthalmic carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

| Interfering RNA | Amount in weight %<br>up to 99; 0.1-99; 0.1-50; 0.5-10.0 |
|---|---|
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 Ml |

| Interfering RNA | Amount in weight %<br>up to 99; 0.1-99; 0.1-50; 0.5-10.0 |
|---|---|
| Phosphate Buffered Saline | 1.0 |
| Benzalkonium Chloride | 0.01 |
| Polysorbate 80 | 0.5 |
| Purified water (RNase-free) | q.s. to 100% |

| Interfering RNA | Amount in weight %<br>up to 99; 0.1-99; 0.1-50; 0.5-10.0 |
|---|---|
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

| Interfering RNA | Amount in weight %<br>up to 99; 0.1-99; 0.1-50; 0.5-10.0 |
|---|---|
| Phosphate Buffered Saline | 1.0 |
| Hydroxypropyl-β-cyclodextrin | 4.0 |
| Purified water (RNase-free) | q.s. to 100% |

In general, the doses of combination compositions as provided herein will vary, but will be in an effective amount, which refers to an amount of a combination of interfering RNAs acting together during an overlapping interval of time, that effectively inhibits or causes regression of neovascularization or angiogenesis, thereby preventing or treating retinal edema, AMD, DR, sequela associated with retinal ischemia, or PSNV, for example, in a human patient.

Generally, an effective amount of the interfering RNAs of embodiments of the invention results in an extracellular concentration at the surface of the target cell of from 100 pM to 100 nM, or from 1 nM to 50 nM, or from 5 nM to about 10 nM, or about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the eye one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with siRNAs directed against FRP-1 mRNA is expected to be beneficial over small molecule topical ocular drops by increasing the duration of action, thereby allowing less frequent dosing and greater patient compliance.

While the precise regimen is left to the discretion of the clinician, interfering RNAs may be administered by placing one drop in each eye as directed by the clinician. An effective amount of a formulation may depend on factors such as the age, race, and sex of the subject, the severity of the ocular hypertension, the rate of target gene transcript/protein turnover, the interfering RNA potency, and the interfering RNA stability, for example. In one embodiment, the interfering RNA is delivered topically to the eye and reaches the trabecular meshwork, retina, or optic nerve head at a therapeutic dose thereby ameliorating a glaucoma disease process.

Acceptable Carriers:

An ophthalmically acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (*Mirus* Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles. Tissue- or cell-specific delivery can be accomplished by the inclusion of an appropriate targeting moiety such as an antibody or antibody fragment.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Ophthalmic solution formulations may be prepared by dissolving the interfering RNA in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art for other ophthalmic formulations. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits:

Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also may contain a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an ophthalmically acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of FRP-1 interfering RNA to knock-down the levels of endogenous FRP-1 expression in, for example, human trabecular meshwork (TM) cells is carried out as follows. Transfection of a transformed human TM cell line designated GTM3 or HTM-3 (see Pang, I. H. et al., 1994. *Curr. Eye Res.* 13:51-63) is accomplished using standard in vitro concentrations of FRP-1 interfering RNA (100 nM) as cited herein and LIPOFECTAMINE™ 2000 (Invitrogen, Carlsbad, Calif.) at a 1:1 (w/v) ratio. Scrambled and lamin A/C siRNA (Dharmacon) are used as controls. QPCR TAQ-MAN® forward and reverse primers and a probe set that encompasses the target site are used to assess the degree of mRNA cleavage. Such primer/probe sets may be synthesized by ABI (Applied Biosystems, Foster City, Calif.), for example. To reduce the chance of non-specific, off-target effects, the lowest possible siRNA concentration for inhibiting FRP-1 mRNA expression is determined for a siRNA. FRP-1 mRNA knock-down is assessed by QPCR amplification using an appropriate primer/probe set. A dose response of FRP-1 siRNA in GTM3 cells is observed in GTM3 cells after 24 hour treatment with 0, 1, 3, 10, 30, and 100 nM dose range of siRNA, for example. Data are fitted using GraphPad Prism 4 software (GraphPad Software, Inc., San Diego, Calif.) with a variable slope, sigmoidal dose response algorithm and a top constraint of 100%. An $IC_{50}$ is obtained for the particular siRNA tested.

Example 1

Interfering RNA for Silencing FRP1

The present study examines the ability of FRP1 interfering RNA to knock-down the levels of endogenous FRP1 mRNA in COS cells.

COS-7 cells were plated at ~20% confluence in 12-well plates the day before transfection. At the time of transfection, the cells appeared to be 50-70% confluent. Cells were harvested 1 and 3 days after transfection. Transfection of a double-stranded FRP1-siRNA having a sense strand sequence 5' AAGAAGAUUGUCCCCAAGAAG 3' (SEQ ID NO:146, which is SEQ ID NO:18 with an added 5'AA; purchased from Dharmacon, Lafayette, Colo.) was carried out using OLIGOFECTAMINE™ (Invitrogen, Carlsbad, Calif.) and 100 nmole of siRNA for each well of 12-well plate in triplicate. The control is without siRNA. RNA extraction was by RNAqueous™ for PCR (Ambion, Austin, Tex.) and cDNA was synthesized with TAQMAN™ reverse transcription agents (PE Biosystems (Applied Biosystems, Foster City, Calif.)). The QPCR was performed using TAQ-MAN™ universal PCR master mix and 7700 SDS (PE Biosystems) in triplicate. Ribosomal RNA (18s, PE Biosystems) was used as a normalization control in the multiplex QPCR. The QPCR data are provided in FIG. 1 and show significant inhibition of FRP1 mRNA at day 1 (22%, P=0.04) and at day 3 (32%, P=0.002) after transfection as compared to controls.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A composition comprising a double strand interfering RNA having a sense strand and an antisense strand wherein both the sense strand and the antisense strand are each 19 to 49 nucleotides in length, and wherein the antisense strand comprises a nucleotide sequence 100% complementary to nucleotides 1-19 of SEQ ID NO:18, SEQ ID NO: 98, or SEQ ID NO: 192; and a pharmaceutically acceptable carrier.

2. The composition of claim 1, wherein the interfering RNA is an shRNA, an siRNA, or an miRNA.

3. The composition of claim 1, further comprising a second interfering RNA targeted to the Frizzled Related Protein-1 mRNA.

4. The composition of claim 1, wherein the sense strand and the antisense strand are connected by a loop.

5. The composition of claim 4, wherein the loop consists of a nucleotide strand.

6. The composition of claim 1, wherein the sense strand contains one or more chemically modified nucleotides, one or more deoxyribonucleotides, and/or one or more non-phosphodiester linkages, and a pharmaceutically acceptable carrier.

7. The composition of claim 1, wherein the antisense strand contains one or more chemically modified nucleotides, one or more deoxyribonucleotides, and/or one or more non-phosphodiester linkages, and a pharmaceutically acceptable carrier.

8. The composition of claim 1, wherein the sense strand and the antisense strand each contains one or more chemically modified nucleotides, one or more deoxyribonucleotides, and/or one or more non-phosphodiester linkages, and a pharmaceutically acceptable carrier.

* * * * *

SEQUENCE LISTING

<160> NUMBER OF SEQ ID NOS: 197

<210> SEQ ID NO 1
<211> LENGTH: 4469
<212> TYPE: DNA
<213> ORGANISM: Homo sapiens

<400> SEQUENCE: 1

```
cctgcagcct ccggagtcag tgccgcgcgc ccgccgcccc gcgccttcct gctcgccgca      60
cctccgggag ccggggcgca cccagcccgc agcgccgcct ccccgcccgc gccgcctccg     120
accgcaggcc gagggccgcc actggccggg gggaccgggc agcagcttgc ggccgcggag     180
ccgggcaacg ctggggactg cgccttttgt ccccggaggt ccctggaagt ttgcggcagg     240
acgcgcgcgg ggaggcggcg gaggcagccc cgacgtcgcg gagaacaggg cgcagagccg     300
gcatgggcat cgggcgcagc gagggggggcc gccgcgggc cctgggcgtg ctgctggcgc     360
tgggcgcggc gcttctggcc gtgggctcgg ccagcgagta cgactacgtg agcttccagt     420
cggacatcgg cccgtaccag agcgggcgct tctacaccaa gccacctcag tgcgtggaca     480
tccccgcgga cctgcggctg tgccacaacg tgggctacaa gaagatggtg ctgcccaacc     540
tgctggagca cgagaccatg gcggaggtga gcagcaggc cagcagctgg gtgccctgc      600 tcaacaagaa ctgccacgcc gggacccagg tcttcctctg ctcgctcttc gcgcccgtct     660
```

```
gcctggaccg gcccatctac ccgtgtcgct ggctctgcga ggccgtgcgc gactcgtgcg     720
agccggtcat gcagttcttc ggcttctact ggcccgagat gcttaagtgt gacaagttcc     780
cggaggggga cgtctgcatc gccatgacgc cgcccaatgc caccgaagcc tccaagcccc     840
aaggcacaac ggtgtgtcct ccctgtgaca acgagttgaa atctgaggcc atcattgaac     900
atctctgtgc cagcgagttt gcactgagga tgaaaataaa agaagtgaaa aagaaaatg      960
gcgacaagaa gattgtcccc aagaagaaga agccctgaa gttggggccc atcaagaaga     1020
aggacctgaa gaagcttgtg ctgtacctga gaatggggc tgactgtccc tgccaccagc     1080
tggcaaccct cagccaccac ttcctcatca tgggccgcaa ggtgaagagc cagtacttgc     1140
tgacggccat ccacaagtgg gacaagaaaa acaaggagtt caaaaacttc atgaagaaaa     1200
tgaaaaacca tgagtgcccc acctttcagt ccgtgtttaa gtgattctcc cgggggcagg     1260
gtggggaggg agcctcgggt ggggtgggag cggggggac agtgcccggg aacccgtggt      1320
cacacacacg cactgccctg tcagtagtgg acattgtaat ccagtcggct tgttcttgca     1380
gcattcccgc tcccttttccc tccatagcca cgctccaaac cccagggtag ccatggccgg    1440
gtaaagcaag ggccatttag attaggaagg ttttaagat ccgcaatgtg gagcagcagc     1500
cactgcacag gaggaggtga caaaccattt ccaacagcaa cacagccact aaaacacaaa     1560
aaggggatt gggcggaaag tgagagccag cagcaaaaac tacattttgc aacttgttgg     1620
tgtggatcta ttggctgatc tatgcctttc aactagaaaa ttctaatgat tggcaagtca     1680
cgttgttttc aggtccagag tagtttcttt ctgtctgctt taaatggaaa cagactcata     1740
ccacacttac aattaaggtc aagcccagaa agtgataagt gcaggagga aaagtgcaag    1800
tccattatct aatagtgaca gcaaagggac caggggagag gcattgcctt ctctgcccac     1860
agtctttccg tgtgattgtc tttgaatctg aatcagccag tctcagatgc cccaaagttt     1920
cggttcctat gagcccgggg catgatctga tccccaagac atgtggaggg gcagcctgtg     1980
cctgcctttg tgtcagaaaa aggaaaccac agtgagcctg agagacgg cgattttcgg      2040
gctgagaagg cagtagtttt caaaacacat agttaaaaaa gaaacaaatg aaaaaaattt     2100
tagaacagtc cagcaaattg ctagtcaggg tgaattgtga aattgggtga agagcttagg     2160
attctaatct catgtttttt cctttcaca ttttaaaag aacaatgaca aacacccact      2220
tattttcaa ggttttaaaa cagtctcat gagcatttg aaaggtgtgc tagaacaagg       2280
tctcctgatc cgtccgaggc tgcttcccag aggagcagct ctccccaggc atttgccaag    2340
ggaggcggat ttccctggta gtgtagctgt gtggcttttcc ttcctgaaga gtccgtggtt   2400
gccctagaac ctaacacccc ctagcaaaac tcacagagct ttccgttttt ttctttcctg    2460
taaagaaaca tttcctttga acttgattgc ctatggatca aagaaattca gaacagcctg    2520
cctgttcccc cgcactttt acatatattt gtttcatttc tgcagatgga agttgacat      2580
gggtggggtg tccccatcca gcgagagagt ttcaaaagca aaacatctct gcagttttc    2640
ccaagtaccc tgagatactt cccaaagccc ttatgtttaa tcagcgatgt atataagcca    2700
gttcacttag acaactttac ccttcttgtc caatgtacag gaagtagttc taaaaaaaat   2760
gcatattaat ttcttccccc aaagccggat tcttaattct ctgcaacact tgaggacat    2820
ttatgattgt ccctctgggc caatgcttat acccagtgag gatgctgcag tgaggctgta   2880
aagtggcccc ctgcggccct agcctgaccc ggagaaagga tggtagattc tgttaactct    2940
tgaagactcc agtatgaaaa tcagcatgcc cgcctagtta cctaccggag agttatcctg   3000
ataaattaac ctctcacagt tagtgatcct gtccttttaa caccttttt gtggggttct    3060
```

-continued

| | |
|---|---|
| ctctgacctt tcatcgtaaa gtgctggga ccttaagtga tttgcctgta attttggatg | 3120 |
| attaaaaaat gtgtatatat attagctaat tagaaatatt ctacttctct gttgtcaaac | 3180 |
| tgaaattcag agcaagttcc tgagtgcgtg gatctgggtc ttagttctgg ttgattcact | 3240 |
| caagagttca gtgctcatac gtatctgctc attttgacaa agtgcctcat gcaaccgggc | 3300 |
| cctctctctg cggcagagtc cttagtggag gggtttacct ggaacataag tagttaccac | 3360 |
| agaatacgga agagcaggtg actgtgctgt gcagctctct aaatgggaat tctcaggtag | 3420 |
| gaagcaacag cttcagaaag agctcaaaat aaattggaaa tgtgaatcgc agctgtgggt | 3480 |
| tttaccaccg tctgtctcag agtcccagga ccttgagtgt cattagttac tttattgaag | 3540 |
| gttttagacc catagcagct ttgtctctgt cacatcagca atttcagaac caaaagggag | 3600 |
| gctctctgta ggcacagagc tgcactatca cgagcctttg ttttctccca caaagtatct | 3660 |
| aacaaaacca atgtgcagac tgattggcct ggtcattggt ctccgagaga ggaggtttgc | 3720 |
| ctgtgatttg cctgtgattt cctaattatc gctagggcca aggtgggatt tgtaaagctt | 3780 |
| tacaataatc attctggata gagtcctggg aggtccttgg cagaactcag ttaaatcttt | 3840 |
| gaagaatatt tgtagttatc ttagaagata gcatgggagg tgaggattcc aaaaacattt | 3900 |
| tatttttaaa atatcctgtg taacacttgg ctcttggtac ctgtgggtta gcatcaagtt | 3960 |
| ctccccaggg tagaattcaa tcagagctcc agtttgcatt tggatgtgta aattacagta | 4020 |
| atcccatttc ccaaacctaa aatctgtttt tctcatcaga ctctgagtaa ctggttgctg | 4080 |
| tgtcataact tcatagatgc aggaggctca ggtgatctgt ttgaggagag caccctaggc | 4140 |
| agcctgcagg gaataacata ctggccgttc tgacctgttg ccagcagata cacaggacat | 4200 |
| ggatgaaatt cccgtttcct ctagtttctt cctgtagtac tcctctttta gatcctaagt | 4260 |
| ctcttacaaa agctttgaat actgtgaaaa tgttttacat tccatttcat ttgtgttgtt | 4320 |
| tttttaactg cattttacca gatgttttga tgttatcgct tatgttaata gtaattcccg | 4380 |
| tacgtgttca ttttatttc atgcttttc agccatgtat caatattcac ttgactaaaa | 4440 |
| tcactcaatt aatcaatgaa aaaaaaaaa | 4469 |

```
<210> SEQ ID NO 2
<211> LENGTH: 19
<212> TYPE: DNA
<213> ORGANISM: Artificial
<220> FEATURE:
<223> OTHER INFORMATION: Target Sequence

<400> SEQUENCE: 2
cgtgggctac aagaagatg                                                    19

<210> SEQ ID NO 3
<211> LENGTH: 21
<212> TYPE: DNA
<213> ORGANISM: Artificial
<220> FEATURE:
<223> OTHER INFORMATION: Sense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 3
cgugggcuac aagaagaugn n                                                 21
```

```
<210> SEQ ID NO 4
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 4
caucuucuug uagcccacgn n                                        21

<210> SEQ ID NO 5
<211> LENGTH: 21
<212> TYPE: RNA
<213> ORGANISM: Artificial
<220> FEATURE:
<223> OTHER INFORMATION: Sense Strand

<400> SEQUENCE: 5
cgugggcuac aagaagaugu u                                        21

<210> SEQ ID NO 6
<211> LENGTH: 21
<212> TYPE: RNA
<213> ORGANISM: Artificial
<220> FEATURE:
<223> OTHER INFORMATION: Antisense Strand

<400> SEQUENCE: 6
caucuucuug uagcccacgu u                                        21

<210> SEQ ID NO 7
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C. G
<220> FEATURE:
<221> NAME/KEY: misc_feature
<222> LOCATION: (28)..(48)
<223> OTHER INFORMATION: ribonucleotides

<400> SEQUENCE: 7
cgugggcuac aagaagaugn nnnnnnncau cuucuuguag cccacguu           48

<210> SEQ ID NO 8
<211> LENGTH: 19
<212> TYPE: DNA
<213> ORGANISM: Artificial
<220> FEATURE:
<223> OTHER INFORMATION: Target Sequence

<400> SEQUENCE: 8
gaagatggtg ctgcccaac                                           19
```

```
<210> SEQ ID NO 9
<211> LENGTH: 19
<212> TYPE: DNA
<213> ORGANISM: Artificial
<220> FEATURE:
<223> OTHER INFORMATION: Target Sequence

<400> SEQUENCE: 9
gatggtgctg cccaacctg                                                  19

<210> SEQ ID NO 10
<211> LENGTH: 19
<212> TYPE: DNA
<213> ORGANISM: Artificial
<220> FEATURE:
<223> OTHER INFORMATION: Target Sequence

<400> SEQUENCE: 10
gtgtgacaag ttcccggag                                                  19

<210> SEQ ID NO 11
<211> LENGTH: 19
<212> TYPE: DNA
<213> ORGANISM: Artificial
<220> FEATURE:
<223> OTHER INFORMATION: Target Sequence

<400> SEQUENCE: 11
tgccaccgaa gcctccaag                                                  19

<210> SEQ ID NO 12
<211> LENGTH: 19
<212> TYPE: DNA
<213> ORGANISM: Artificial
<220> FEATURE:
<223> OTHER INFORMATION: Target Sequence

<400> SEQUENCE: 12
ggcacaacgg tgtgtcctc                                                  19

<210> SEQ ID NO 13
<211> LENGTH: 19
<212> TYPE: DNA
<213> ORGANISM: Artificial
<220> FEATURE:
<223> OTHER INFORMATION: Target Sequence

<400> SEQUENCE: 13
cggtgtgtcc tccctgtga                                                  19

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
cgagttgaaa tctgaggcc                                                  19

<210> SEQ ID NO 15
<211> LENGTH: 19
<212> TYPE: DNA
<213> ORGANISM: Artificial
<220> FEATURE:
<223> OTHER INFORMATION: Target Sequence
```

```
<400> SEQUENCE: 15
atctgaggcc atcattgaa                                                19

<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
catctctgtg ccagcgagt                                                19

<210> SEQ ID NO 17
<211> LENGTH: 19
<212> TYPE: DNA
<213> ORGANISM: Artificial
<220> FEATURE:
<223> OTHER INFORMATION: Target Sequence

<400> SEQUENCE: 17
tggcgacaag aagattgtc                                                19

<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
gaagattgtc cccaagaag                                                19

<210> SEQ ID NO 19
<211> LENGTH: 19
<212> TYPE: DNA
<213> ORGANISM: Artificial
<220> FEATURE:
<223> OTHER INFORMATION: Target Sequence

<400> SEQUENCE: 19
gattgtcccc aagaagaag                                                19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
gaagaagaag cccctgaag                                                19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
gaagaagccc ctgaagttg                                                19

<210> SEQ ID NO 22
<211> LENGTH: 19
```

```
<212> TYPE: DNA
<213> ORGANISM: Artificial
<220> FEATURE:
<223> OTHER INFORMATION: Target Sequence

<400> SEQUENCE: 22
gaagcccctg aagttgggg                                                    19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
gttggggccc atcaagaag                                                    19

<210> SEQ ID NO 24
<211> LENGTH: 19
<212> TYPE: DNA
<213> ORGANISM: Artificial
<220> FEATURE:
<223> OTHER INFORMATION: Target Sequence

<400> SEQUENCE: 24
gaagaaggac ctgaagaag                                                    19

<210> SEQ ID NO 25
<211> LENGTH: 19
<212> TYPE: DNA
<213> ORGANISM: Artificial
<220> FEATURE:
<223> OTHER INFORMATION: Target Sequence

<400> SEQUENCE: 25
gaaggacctg aagaagctt                                                    19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
ggacctgaag aagcttgtg                                                    19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
gaagcttgtg ctgtacctg                                                    19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
```
gcttgtgctg tacctgaag                                                   19

<210> SEQ ID NO 29
<211> LENGTH: 19
<212> TYPE: DNA
<213> ORGANISM: Artificial
<220> FEATURE:
<223> OTHER INFORMATION: Target Sequence

<400> SEQUENCE: 29
gaatggggct gactgtccc                                                   19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
cctcagccac cacttcctc                                                   19

<210> SEQ ID NO 31
<211> LENGTH: 19
<212> TYPE: DNA
<213> ORGANISM: Artificial
<220> FEATURE:
<223> OTHER INFORMATION: Target Sequence

<400> SEQUENCE: 31
ggtgaagagc cagtacttg                                                   19

<210> SEQ ID NO 32
<211> LENGTH: 19
<212> TYPE: DNA
<213> ORGANISM: Artificial
<220> FEATURE:
<223> OTHER INFORMATION: Target Sequence

<400> SEQUENCE: 32
gagccagtac ttgctgacg                                                   19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
accatgagtg ccccacctt                                                   19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
tccagtcggc ttgttcttg                                                   19

<210> SEQ ID NO 35
<211> LENGTH: 19
<212> TYPE: DNA
<213> ORGANISM: Artificial

<220> FEATURE:
<223> OTHER INFORMATION: Target Sequence

<400> SEQUENCE: 35
agcaagggcc atttagatt                    19

<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
gggccattta gattaggaa                    19

<210> SEQ ID NO 37
<211> LENGTH: 19
<212> TYPE: DNA
<213> ORGANISM: Artificial
<220> FEATURE:
<223> OTHER INFORMATION: Target Sequence

<400> SEQUENCE: 37
gatccgcaat gtggagcag                    19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
tgtggagcag cagccactg                    19

<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
accatttcca acagcaaca                    19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
cagcaacaca gccactaaa                    19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41 aggggattg ggcggaaag                     19

```
<210> SEQ ID NO 42
<211> LENGTH: 19
<212> TYPE: DNA
<213> ORGANISM: Artificial
<220> FEATURE:
<223> OTHER INFORMATION: Target Sequence

<400> SEQUENCE: 42
agtgagagcc agcagcaaa                                                  19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
cttgttggtg tggatctat                                                  19

<210> SEQ ID NO 44
<211> LENGTH: 19
<212> TYPE: DNA
<213> ORGANISM: Artificial
<220> FEATURE:
<223> OTHER INFORMATION: Target Sequence

<400> SEQUENCE: 44
ttctaatgat tggcaagtc                                                  19

<210> SEQ ID NO 45
<211> LENGTH: 19
<212> TYPE: DNA
<213> ORGANISM: Artificial
<220> FEATURE:
<223> OTHER INFORMATION: Target Sequence

<400> SEQUENCE: 45
tgattggcaa gtcacgttg                                                  19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
atggaaacag actcatacc                                                  19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
acagactcat accacactt                                                  19

<210> SEQ ID NO 48
<211> LENGTH: 19
<212> TYPE: DNA
<213> ORGANISM: Artificial
<220> FEATURE:
<223> OTHER INFORMATION: Target Sequence
```

<400> SEQUENCE: 48
ttaaggtcaa gcccagaaa                           19

<210> SEQ ID NO 49
<211> LENGTH: 19
<212> TYPE: DNA
<213> ORGANISM: Artificial
<220> FEATURE:
<223> OTHER INFORMATION: Target Sequence

<400> SEQUENCE: 49
ggtcaagccc agaaagtga                           19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
gcccagaaag tgataagtg                           19

<210> SEQ ID NO 51
<211> LENGTH: 19
<212> TYPE: DNA
<213> ORGANISM: Artificial
<220> FEATURE:
<223> OTHER INFORMATION: Target Sequence

<400> SEQUENCE: 51
agtgataagt gcagggagg                           19

<210> SEQ ID NO 52
<211> LENGTH: 19
<212> TYPE: DNA
<213> ORGANISM: Artificial
<220> FEATURE:
<223> OTHER INFORMATION: Target Sequence

<400> SEQUENCE: 52
gtgcaagtcc attatctaa                           19

<210> SEQ ID NO 53
<211> LENGTH: 19
<212> TYPE: DNA
<213> ORGANISM: Artificial
<220> FEATURE:
<223> OTHER INFORMATION: Target Sequence

<400> SEQUENCE: 53
gtccattatc taatagtga                           19

<210> SEQ ID NO 54
<211> LENGTH: 19
<212> TYPE: DNA
<213> ORGANISM: Artificial
<220> FEATURE:
<223> OTHER INFORMATION: Target Sequence

<400> SEQUENCE: 54
tagtgacagc aaagggacc                           19

<210> SEQ ID NO 55

```
<211> LENGTH: 19
<212> TYPE: DNA
<213> ORGANISM: Artificial
<220> FEATURE:
<223> OTHER INFORMATION: Target Sequence

<400> SEQUENCE: 55
tctgaatcag ccagtctca                                                  19

<210> SEQ ID NO 56
<211> LENGTH: 19
<212> TYPE: DNA
<213> ORGANISM: Artificial
<220> FEATURE:
<223> OTHER INFORMATION: Target Sequence

<400> SEQUENCE: 56
tcagccagtc tcagatgcc                                                  19

<210> SEQ ID NO 57
<211> LENGTH: 19
<212> TYPE: DNA
<213> ORGANISM: Artificial
<220> FEATURE:
<223> OTHER INFORMATION: Target Sequence

<400> SEQUENCE: 57
agtttcggtt cctatgagc                                                  19

<210> SEQ ID NO 58
<211> LENGTH: 19
<212> TYPE: DNA
<213> ORGANISM: Artificial
<220> FEATURE:
<223> OTHER INFORMATION: Target Sequence

<400> SEQUENCE: 58
aggaaaccac agtgagcct                                                  19

<210> SEQ ID NO 59
<211> LENGTH: 19
<212> TYPE: DNA
<213> ORGANISM: Artificial
<220> FEATURE:
<223> OTHER INFORMATION: Target Sequence

<400> SEQUENCE: 59
accacagtga gcctgagag                                                  19

<210> SEQ ID NO 60
<211> LENGTH: 19
<212> TYPE: DNA
<213> ORGANISM: Artificial
<220> FEATURE:
<223> OTHER INFORMATION: Target Sequence

<400> SEQUENCE: 60
cagtccagca aattgctag                                                  19

<210> SEQ ID NO 61
<211> LENGTH: 19
<212> TYPE: DNA
<213> ORGANISM: Artificial
<220> FEATURE:
<223> OTHER INFORMATION: Target Sequence

<400> SEQUENCE: 61
```

```
attgctagtc agggtgaat                                                    19

<210> SEQ ID NO 62
<211> LENGTH: 19
<212> TYPE: DNA
<213> ORGANISM: Artificial
<220> FEATURE:
<223> OTHER INFORMATION: Target Sequence

<400> SEQUENCE: 62
ttgtgaaatt gggtgaaga                                                    19

<210> SEQ ID NO 63
<211> LENGTH: 19
<212> TYPE: DNA
<213> ORGANISM: Artificial
<220> FEATURE:
<223> OTHER INFORMATION: Target Sequence

<400> SEQUENCE: 63
attgggtgaa gagcttagg                                                    19

<210> SEQ ID NO 64
<211> LENGTH: 19
<212> TYPE: DNA
<213> ORGANISM: Artificial
<220> FEATURE:
<223> OTHER INFORMATION: Target Sequence

<400> SEQUENCE: 64
gagcttagga ttctaatct                                                    19

<210> SEQ ID NO 65
<211> LENGTH: 19
<212> TYPE: DNA
<213> ORGANISM: Artificial
<220> FEATURE:
<223> OTHER INFORMATION: Target Sequence

<400> SEQUENCE: 65
gaacaatgac aaacaccca                                                    19

<210> SEQ ID NO 66
<211> LENGTH: 19
<212> TYPE: DNA
<213> ORGANISM: Artificial
<220> FEATURE:
<223> OTHER INFORMATION: Target Sequence

<400> SEQUENCE: 66
caatgacaaa cacccactt                                                    19

<210> SEQ ID NO 67
<211> LENGTH: 19
<212> TYPE: DNA
<213> ORGANISM: Artificial
<220> FEATURE:
<223> OTHER INFORMATION: Target Sequence

<400> SEQUENCE: 67
tgacaaacac ccacttatt                                                    19

<210> SEQ ID NO 68
<211> LENGTH: 19
<212> TYPE: DNA
```

```
<213> ORGANISM: Artificial
<220> FEATURE:
<223> OTHER INFORMATION: Target Sequence

<400> SEQUENCE: 68
cagtctacat tgagcattt                                                 19

<210> SEQ ID NO 69
<211> LENGTH: 19
<212> TYPE: DNA
<213> ORGANISM: Artificial
<220> FEATURE:
<223> OTHER INFORMATION: Target Sequence

<400> SEQUENCE: 69
aggtgtgcta gaacaaggt                                                 19

<210> SEQ ID NO 70
<211> LENGTH: 19
<212> TYPE: DNA
<213> ORGANISM: Artificial
<220> FEATURE:
<223> OTHER INFORMATION: Target Sequence

<400> SEQUENCE: 70
caaggtctcc tgatccgtc                                                 19

<210> SEQ ID NO 71
<211> LENGTH: 19
<212> TYPE: DNA
<213> ORGANISM: Artificial
<220> FEATURE:
<223> OTHER INFORMATION: Target Sequence

<400> SEQUENCE: 71
ggtctcctga tccgtccga                                                 19

<210> SEQ ID NO 72
<211> LENGTH: 19
<212> TYPE: DNA
<213> ORGANISM: Artificial
<220> FEATURE:
<223> OTHER INFORMATION: Target Sequence

<400> SEQUENCE: 72
gagtccgtgg ttgccctag                                                 19

<210> SEQ ID NO 73
<211> LENGTH: 19
<212> TYPE: DNA
<213> ORGANISM: Artificial
<220> FEATURE:
<223> OTHER INFORMATION: Target Sequence

<400> SEQUENCE: 73
cctaacaccc cctagcaaa                                                 19

<210> SEQ ID NO 74
<211> LENGTH: 19
<212> TYPE: DNA
<213> ORGANISM: Artificial
<220> FEATURE:
<223> OTHER INFORMATION: Target Sequence

<400> SEQUENCE: 74
ctcacagagc tttccgttt                                                 19
```

<210> SEQ ID NO 75
<211> LENGTH: 19
<212> TYPE: DNA
<213> ORGANISM: Artificial
<220> FEATURE:
<223> OTHER INFORMATION: Target Sequence

<400> SEQUENCE: 75
agaaacattt cctttgaac                                                  19

<210> SEQ ID NO 76
<211> LENGTH: 19
<212> TYPE: DNA
<213> ORGANISM: Artificial
<220> FEATURE:
<223> OTHER INFORMATION: Target Sequence

<400> SEQUENCE: 76
acatttcctt tgaacttga                                                  19

<210> SEQ ID NO 77
<211> LENGTH: 19
<212> TYPE: DNA
<213> ORGANISM: Artificial
<220> FEATURE:
<223> OTHER INFORMATION: Target Sequence

<400> SEQUENCE: 77
cttgattgcc tatggatca                                                  19

<210> SEQ ID NO 78
<211> LENGTH: 19
<212> TYPE: DNA
<213> ORGANISM: Artificial
<220> FEATURE:
<223> OTHER INFORMATION: Target Sequence

<400> SEQUENCE: 78
agaaattcag aacagcctg                                                  19

<210> SEQ ID NO 79
<211> LENGTH: 19
<212> TYPE: DNA
<213> ORGANISM: Artificial
<220> FEATURE:
<223> OTHER INFORMATION: Target Sequence

<400> SEQUENCE: 79
attcagaaca gcctgcctg                                                  19

<210> SEQ ID NO 80
<211> LENGTH: 19
<212> TYPE: DNA
<213> ORGANISM: Artificial
<220> FEATURE:
<223> OTHER INFORMATION: Target Sequence

<400> SEQUENCE: 80
agttgacatg ggtggggtg                                                  19

<210> SEQ ID NO 81
<211> LENGTH: 19
<212> TYPE: DNA
<213> ORGANISM: Artificial
<220> FEATURE:

<223> OTHER INFORMATION: Target Sequence

<400> SEQUENCE: 81
gtaccctgag atacttccc                                                    19

<210> SEQ ID NO 82
<211> LENGTH: 19
<212> TYPE: DNA
<213> ORGANISM: Artificial
<220> FEATURE:
<223> OTHER INFORMATION: Target Sequence

<400> SEQUENCE: 82
agcccttatg tttaatcag                                                    19

<210> SEQ ID NO 83
<211> LENGTH: 19
<212> TYPE: DNA
<213> ORGANISM: Artificial
<220> FEATURE:
<223> OTHER INFORMATION: Target Sequence

<400> SEQUENCE: 83
tcagcgatgt atataagcc                                                    19

<210> SEQ ID NO 84
<211> LENGTH: 19
<212> TYPE: DNA
<213> ORGANISM: Artificial
<220> FEATURE:
<223> OTHER INFORMATION: Target Sequence

<400> SEQUENCE: 84
gccagttcac ttagacaac                                                    19

<210> SEQ ID NO 85
<211> LENGTH: 19
<212> TYPE: DNA
<213> ORGANISM: Artificial
<220> FEATURE:
<223> OTHER INFORMATION: Target Sequence

<400> SEQUENCE: 85 ctttacccctt cttgtccaa                                                   19

<210> SEQ ID NO 86
<211> LENGTH: 19
<212> TYPE: DNA
<213> ORGANISM: Artificial
<220> FEATURE:
<223> OTHER INFORMATION: Target Sequence

<400> SEQUENCE: 86
tgtacaggaa gtagttcta                                                    19

<210> SEQ ID NO 87
<211> LENGTH: 19
<212> TYPE: DNA
<213> ORGANISM: Artificial
<220> FEATURE:
<223> OTHER INFORMATION: Target Sequence

<400> SEQUENCE: 87
tgcatattaa tttcttccc                                                    19

```
<210> SEQ ID NO 88
<211> LENGTH: 19
<212> TYPE: DNA
<213> ORGANISM: Artificial
<220> FEATURE:
<223> OTHER INFORMATION: Target Sequence

<400> SEQUENCE: 88
tttcttcccc caaagccgg                                                19

<210> SEQ ID NO 89
<211> LENGTH: 19
<212> TYPE: DNA
<213> ORGANISM: Artificial
<220> FEATURE:
<223> OTHER INFORMATION: Target Sequence

<400> SEQUENCE: 89
agccggattc ttaattctc                                                19

<210> SEQ ID NO 90
<211> LENGTH: 19
<212> TYPE: DNA
<213> ORGANISM: Artificial
<220> FEATURE:
<223> OTHER INFORMATION: Target Sequence

<400> SEQUENCE: 90
ttctctgcaa cactttgag                                                19

<210> SEQ ID NO 91
<211> LENGTH: 19
<212> TYPE: DNA
<213> ORGANISM: Artificial
<220> FEATURE:
<223> OTHER INFORMATION: Target Sequence

<400> SEQUENCE: 91
cactttgagg acatttatg                                                19

<210> SEQ ID NO 92
<211> LENGTH: 19
<212> TYPE: DNA
<213> ORGANISM: Artificial
<220> FEATURE:
<223> OTHER INFORMATION: Target Sequence

<400> SEQUENCE: 92
tgcttatacc cagtgagga                                                19

<210> SEQ ID NO 93
<211> LENGTH: 19
<212> TYPE: DNA
<213> ORGANISM: Artificial
<220> FEATURE:
<223> OTHER INFORMATION: Target Sequence

<400> SEQUENCE: 93
aggatggtag attctgtta                                                19

<210> SEQ ID NO 94
<211> LENGTH: 19
<212> TYPE: DNA
<213> ORGANISM: Artificial
<220> FEATURE:
<223> OTHER INFORMATION: Target Sequence
```

```
<400> SEQUENCE: 94
ctcttgaaga ctccagtat                                               19

<210> SEQ ID NO 95
<211> LENGTH: 19
<212> TYPE: DNA
<213> ORGANISM: Artificial
<220> FEATURE:
<223> OTHER INFORMATION: Target Sequence

<400> SEQUENCE: 95
tcagcatgcc cgcctagtt                                               19

<210> SEQ ID NO 96
<211> LENGTH: 19
<212> TYPE: DNA
<213> ORGANISM: Artificial
<220> FEATURE:
<223> OTHER INFORMATION: Target Sequence

<400> SEQUENCE: 96
attaacctct cacagttag                                               19

<210> SEQ ID NO 97
<211> LENGTH: 19
<212> TYPE: DNA
<213> ORGANISM: Artificial
<220> FEATURE:
<223> OTHER INFORMATION: Target Sequence

<400> SEQUENCE: 97
cctctcacag ttagtgatc                                               19

<210> SEQ ID NO 98
<211> LENGTH: 19
<212> TYPE: DNA
<213> ORGANISM: Artificial
<220> FEATURE:
<223> OTHER INFORMATION: Target Sequence

<400> SEQUENCE: 98
agtgctgggg accttaagt                                               19

<210> SEQ ID NO 99
<211> LENGTH: 19
<212> TYPE: DNA
<213> ORGANISM: Artificial
<220> FEATURE:
<223> OTHER INFORMATION: Target Sequence

<400> SEQUENCE: 99
tgtgtatata tattagcta                                               19

<210> SEQ ID NO 100
<211> LENGTH: 19
<212> TYPE: DNA
<213> ORGANISM: Artificial
<220> FEATURE:
<223> OTHER INFORMATION: Target Sequence

<400> SEQUENCE: 100
ttagaaatat tctacttct                                               19

<210> SEQ ID NO 101
<211> LENGTH: 19
```

```
<212> TYPE: DNA
<213> ORGANISM: Artificial
<220> FEATURE:
<223> OTHER INFORMATION: Target Sequence

<400> SEQUENCE: 101
atattctact tctctgttg                                               19

<210> SEQ ID NO 102
<211> LENGTH: 19
<212> TYPE: DNA
<213> ORGANISM: Artificial
<220> FEATURE:
<223> OTHER INFORMATION: Target Sequence

<400> SEQUENCE: 102
actgaaattc agagcaagt                                               19

<210> SEQ ID NO 103
<211> LENGTH: 19
<212> TYPE: DNA
<213> ORGANISM: Artificial
<220> FEATURE:
<223> OTHER INFORMATION: Target Sequence

<400> SEQUENCE: 103
attcagagca agttcctga                                               19

<210> SEQ ID NO 104
<211> LENGTH: 19
<212> TYPE: DNA
<213> ORGANISM: Artificial
<220> FEATURE:
<223> OTHER INFORMATION: Target Sequence

<400> SEQUENCE: 104
gttcctgagt gcgtggatc                                               19

<210> SEQ ID NO 105
<211> LENGTH: 19
<212> TYPE: DNA
<213> ORGANISM: Artificial
<220> FEATURE:
<223> OTHER INFORMATION: Target Sequence

<400> SEQUENCE: 105
gagttcagtg ctcatacgt                                               19

<210> SEQ ID NO 106
<211> LENGTH: 19
<212> TYPE: DNA
<213> ORGANISM: Artificial
<220> FEATURE:
<223> OTHER INFORMATION: Target Sequence

<400> SEQUENCE: 106
agtgcctcat gcaaccggg                                               19

<210> SEQ ID NO 107
<211> LENGTH: 19
<212> TYPE: DNA
<213> ORGANISM: Artificial
<220> FEATURE:
<223> OTHER INFORMATION: Target Sequence

<400> SEQUENCE: 107
```
cataagtagt taccacaga                                            19

<210> SEQ ID NO 108
<211> LENGTH: 19
<212> TYPE: DNA
<213> ORGANISM: Artificial
<220> FEATURE:
<223> OTHER INFORMATION: Target Sequence

<400> SEQUENCE: 108
gtagttacca cagaatacg                                            19

<210> SEQ ID NO 109
<211> LENGTH: 19
<212> TYPE: DNA
<213> ORGANISM: Artificial
<220> FEATURE:
<223> OTHER INFORMATION: Target Sequence

<400> SEQUENCE: 109
tacggaagag caggtgact                                            19

<210> SEQ ID NO 110
<211> LENGTH: 19
<212> TYPE: DNA
<213> ORGANISM: Artificial
<220> FEATURE:
<223> OTHER INFORMATION: Target Sequence

<400> SEQUENCE: 110
gagcaggtga ctgtgctgt                                            19

<210> SEQ ID NO 111
<211> LENGTH: 19
<212> TYPE: DNA
<213> ORGANISM: Artificial
<220> FEATURE:
<223> OTHER INFORMATION: Target Sequence

<400> SEQUENCE: 111
atgggaattc tcaggtagg                                            19

<210> SEQ ID NO 112
<211> LENGTH: 19
<212> TYPE: DNA
<213> ORGANISM: Artificial
<220> FEATURE:
<223> OTHER INFORMATION: Target Sequence

<400> SEQUENCE: 112
ttctcaggta ggaagcaac                                            19

<210> SEQ ID NO 113
<211> LENGTH: 19
<212> TYPE: DNA
<213> ORGANISM: Artificial
<220> FEATURE:
<223> OTHER INFORMATION: Target Sequence

<400> SEQUENCE: 113
gcaacagctt cagaaagag                                            19

<210> SEQ ID NO 114
<211> LENGTH: 19
<212> TYPE: DNA
<213> ORGANISM: Artificial

```
<220> FEATURE:
<223> OTHER INFORMATION: Target Sequence

<400> SEQUENCE: 114
cagcttcaga aagagctca                                                  19

<210> SEQ ID NO 115
<211> LENGTH: 19
<212> TYPE: DNA
<213> ORGANISM: Artificial
<220> FEATURE:
<223> OTHER INFORMATION: Target Sequence

<400> SEQUENCE: 115
taaattggaa atgtgaatc                                                  19

<210> SEQ ID NO 116
<211> LENGTH: 19
<212> TYPE: DNA
<213> ORGANISM: Artificial
<220> FEATURE:
<223> OTHER INFORMATION: Target Sequence

<400> SEQUENCE: 116
attggaaatg tgaatcgca                                                  19

<210> SEQ ID NO 117
<211> LENGTH: 19
<212> TYPE: DNA
<213> ORGANISM: Artificial
<220> FEATURE:
<223> OTHER INFORMATION: Target Sequence

<400> SEQUENCE: 117
atgtgaatcg cagctgtgg                                                  19

<210> SEQ ID NO 118
<211> LENGTH: 19
<212> TYPE: DNA
<213> ORGANISM: Artificial
<220> FEATURE:
<223> OTHER INFORMATION: Target Sequence

<400> SEQUENCE: 118
gggaggctct ctgtaggca                                                  19

<210> SEQ ID NO 119
<211> LENGTH: 19
<212> TYPE: DNA
<213> ORGANISM: Artificial
<220> FEATURE:
<223> OTHER INFORMATION: Target Sequence

<400> SEQUENCE: 119
ccaatgtgca gactgattg                                                  19

<210> SEQ ID NO 120
<211> LENGTH: 19
<212> TYPE: DNA
<213> ORGANISM: Artificial
<220> FEATURE:
<223> OTHER INFORMATION: Target Sequence

<400> SEQUENCE: 120
tgtgcagact gattggcct                                                  19
```

```
<210> SEQ ID NO 121
<211> LENGTH: 19
<212> TYPE: DNA
<213> ORGANISM: Artificial
<220> FEATURE:
<223> OTHER INFORMATION: Target Sequence

<400> SEQUENCE: 121
ttatcgctag ggccaaggt                                                   19

<210> SEQ ID NO 122
<211> LENGTH: 19
<212> TYPE: DNA
<213> ORGANISM: Artificial
<220> FEATURE:
<223> OTHER INFORMATION: Target Sequence

<400> SEQUENCE: 122
ggtgggattt gtaaagctt                                                   19

<210> SEQ ID NO 123
<211> LENGTH: 19
<212> TYPE: DNA
<213> ORGANISM: Artificial
<220> FEATURE:
<223> OTHER INFORMATION: Target Sequence

<400> SEQUENCE: 123
agctttacaa taatcattc                                                   19

<210> SEQ ID NO 124
<211> LENGTH: 19
<212> TYPE: DNA
<213> ORGANISM: Artificial
<220> FEATURE:
<223> OTHER INFORMATION: Target Sequence

<400> SEQUENCE: 124
taatcattct ggatagagt                                                   19

<210> SEQ ID NO 125
<211> LENGTH: 19
<212> TYPE: DNA
<213> ORGANISM: Artificial
<220> FEATURE:
<223> OTHER INFORMATION: Target Sequence

<400> SEQUENCE: 125
tcattctgga tagagtcct                                                   19

<210> SEQ ID NO 126
<211> LENGTH: 19
<212> TYPE: DNA
<213> ORGANISM: Artificial
<220> FEATURE:
<223> OTHER INFORMATION: Target Sequence

<400> SEQUENCE: 126
ctcagttaaa tctttgaag                                                   19

<210> SEQ ID NO 127
<211> LENGTH: 19
<212> TYPE: DNA
<213> ORGANISM: Artificial
<220> FEATURE:
<223> OTHER INFORMATION: Target Sequence
```

<400> SEQUENCE: 127
atctttgaag aatatttgt                                              19

<210> SEQ ID NO 128
<211> LENGTH: 19
<212> TYPE: DNA
<213> ORGANISM: Artificial
<220> FEATURE:
<223> OTHER INFORMATION: Target Sequence

<400> SEQUENCE: 128
gaatatttgt agttatctt                                              19

<210> SEQ ID NO 129
<211> LENGTH: 19
<212> TYPE: DNA
<213> ORGANISM: Artificial
<220> FEATURE:
<223> OTHER INFORMATION: Target Sequence

<400> SEQUENCE: 129
tatttgtagt tatcttaga                                              19

<210> SEQ ID NO 130
<211> LENGTH: 19
<212> TYPE: DNA
<213> ORGANISM: Artificial
<220> FEATURE:
<223> OTHER INFORMATION: Target Sequence

<400> SEQUENCE: 130
gatagcatgg gaggtgagg                                              19

<210> SEQ ID NO 131
<211> LENGTH: 19
<212> TYPE: DNA
<213> ORGANISM: Artificial
<220> FEATURE:
<223> OTHER INFORMATION: Target Sequence

<400> SEQUENCE: 131
tatcctgtgt aacacttgg                                              19

<210> SEQ ID NO 132
<211> LENGTH: 19
<212> TYPE: DNA
<213> ORGANISM: Artificial
<220> FEATURE:
<223> OTHER INFORMATION: Target Sequence

<400> SEQUENCE: 132
cacttggctc ttggtacct                                              19

<210> SEQ ID NO 133
<211> LENGTH: 19
<212> TYPE: DNA
<213> ORGANISM: Artificial
<220> FEATURE:
<223> OTHER INFORMATION: Target Sequence

<400> SEQUENCE: 133
gttctcccca gggtagaat                                              19

<210> SEQ ID NO 134

```
<211> LENGTH: 19
<212> TYPE: DNA
<213> ORGANISM: Artificial
<220> FEATURE:
<223> OTHER INFORMATION: Target Sequence

<400> SEQUENCE: 134
ttcaatcaga gctccagtt                                                        19

<210> SEQ ID NO 135
<211> LENGTH: 19
<212> TYPE: DNA
<213> ORGANISM: Artificial
<220> FEATURE:
<223> OTHER INFORMATION: Target Sequence

<400> SEQUENCE: 135
tcagagctcc agtttgcat                                                        19

<210> SEQ ID NO 136
<211> LENGTH: 19
<212> TYPE: DNA
<213> ORGANISM: Artificial
<220> FEATURE:
<223> OTHER INFORMATION: Target Sequence

<400> SEQUENCE: 136
attacagtaa tcccatttc                                                        19

<210> SEQ ID NO 137
<211> LENGTH: 19
<212> TYPE: DNA
<213> ORGANISM: Artificial
<220> FEATURE:
<223> OTHER INFORMATION: Target Sequence

<400> SEQUENCE: 137
tcccatttcc caaacctaa                                                        19

<210> SEQ ID NO 138
<211> LENGTH: 19
<212> TYPE: DNA
<213> ORGANISM: Artificial
<220> FEATURE:
<223> OTHER INFORMATION: Target Sequence

<400> SEQUENCE: 138
ctggttgctg tgtcataac                                                        19

<210> SEQ ID NO 139
<211> LENGTH: 19
<212> TYPE: DNA
<213> ORGANISM: Artificial
<220> FEATURE:
<223> OTHER INFORMATION: Target Sequence

<400> SEQUENCE: 139
cttcatagat gcaggaggc                                                        19

<210> SEQ ID NO 140
<211> LENGTH: 19
<212> TYPE: DNA
<213> ORGANISM: Artificial
<220> FEATURE:
<223> OTHER INFORMATION: Target Sequence

<400> SEQUENCE: 140
```

| | |
|---|---|
| taacatactg gccgttctg | 19 |

<210> SEQ ID NO 141
<211> LENGTH: 19
<212> TYPE: DNA
<213> ORGANISM: Artificial
<220> FEATURE:
<223> OTHER INFORMATION: Target Sequence

<400> SEQUENCE: 141

| | |
|---|---|
| catactggcc gttctgacc | 19 |

<210> SEQ ID NO 142
<211> LENGTH: 19
<212> TYPE: DNA
<213> ORGANISM: Artificial
<220> FEATURE:
<223> OTHER INFORMATION: Target Sequence

<400> SEQUENCE: 142

| | |
|---|---|
| attcccgttt cctctagtt | 19 |

<210> SEQ ID NO 143
<211> LENGTH: 19
<212> TYPE: DNA
<213> ORGANISM: Artificial
<220> FEATURE:
<223> OTHER INFORMATION: Target Sequence

<400> SEQUENCE: 143

| | |
|---|---|
| tagtaattcc cgtacgtgt | 19 |

<210> SEQ ID NO 144
<211> LENGTH: 19
<212> TYPE: DNA
<213> ORGANISM: Artificial
<220> FEATURE:
<223> OTHER INFORMATION: Target Sequence

<400> SEQUENCE: 144

| | |
|---|---|
| ttcccgtacg tgttcattt | 19 |

<210> SEQ ID NO 145
<211> LENGTH: 19
<212> TYPE: DNA
<213> ORGANISM: Artificial
<220> FEATURE:
<223> OTHER INFORMATION: Target Sequence

<400> SEQUENCE: 145

| | |
|---|---|
| tcactcaatt aatcaatga | 19 |

<210> SEQ ID NO 146
<211> LENGTH: 21
<212> TYPE: DNA
<213> ORGANISM: Artificial
<220> FEATURE:
<223> OTHER INFORMATION: Target Sequence

<400> SEQUENCE: 146

| | |
|---|---|
| aagaagattg tccccaagaa g | 21 |

<210> SEQ ID NO 147
<211> LENGTH: 19
<212> TYPE: DNA

```
<213> ORGANISM: Artificial
<220> FEATURE:
<223> OTHER INFORMATION: Target Sequence

<400> SEQUENCE: 147
gtgagcttcc agtcggaca                                                19

<210> SEQ ID NO 148
<211> LENGTH: 19
<212> TYPE: DNA
<213> ORGANISM: Artificial
<220> FEATURE:
<223> OTHER INFORMATION: Target Sequence

<400> SEQUENCE: 148
tgagcttcca gtcggacat                                                19

<210> SEQ ID NO 149
<211> LENGTH: 19
<212> TYPE: DNA
<213> ORGANISM: Artificial
<220> FEATURE:
<223> OTHER INFORMATION: Target Sequence

<400> SEQUENCE: 149
cacctcagtg cgtggacat                                                19

<210> SEQ ID NO 150
<211> LENGTH: 19
<212> TYPE: DNA
<213> ORGANISM: Artificial
<220> FEATURE:
<223> OTHER INFORMATION: Target Sequence

<400> SEQUENCE: 150
ccgagatgct taagtgtga                                                19

<210> SEQ ID NO 151
<211> LENGTH: 19
<212> TYPE: DNA
<213> ORGANISM: Artificial
<220> FEATURE:
<223> OTHER INFORMATION: Target Sequence

<400> SEQUENCE: 151
cctgtgacaa cgagttgaa                                                19

<210> SEQ ID NO 152
<211> LENGTH: 19
<212> TYPE: DNA
<213> ORGANISM: Artificial
<220> FEATURE:
<223> OTHER INFORMATION: Target Sequence

<400> SEQUENCE: 152
ctgtgacaac gagttgaaa                                                19

<210> SEQ ID NO 153
<211> LENGTH: 19
<212> TYPE: DNA
<213> ORGANISM: Artificial
<220> FEATURE:
<223> OTHER INFORMATION: Target Sequence

<400> SEQUENCE: 153
tgtgacaacg agttgaaat                                                19
```

```
<210> SEQ ID NO 154
<211> LENGTH: 19
<212> TYPE: DNA
<213> ORGANISM: Artificial
<220> FEATURE:
<223> OTHER INFORMATION: Target Sequence

<400> SEQUENCE: 154
acaacgagtt gaaatctga                                               19

<210> SEQ ID NO 155
<211> LENGTH: 19
<212> TYPE: DNA
<213> ORGANISM: Artificial
<220> FEATURE:
<223> OTHER INFORMATION: Target Sequence

<400> SEQUENCE: 155
agttgaaatc tgaggccat                                               19

<210> SEQ ID NO 156
<211> LENGTH: 19
<212> TYPE: DNA
<213> ORGANISM: Artificial
<220> FEATURE:
<223> OTHER INFORMATION: Target Sequence

<400> SEQUENCE: 156
gccagcgagt ttgcactga                                               19

<210> SEQ ID NO 157
<211> LENGTH: 19
<212> TYPE: DNA
<213> ORGANISM: Artificial
<220> FEATURE:
<223> OTHER INFORMATION: Target Sequence

<400> SEQUENCE: 157
gcgagtttgc actgaggat                                               19

<210> SEQ ID NO 158
<211> LENGTH: 19
<212> TYPE: DNA
<213> ORGANISM: Artificial
<220> FEATURE:
<223> OTHER INFORMATION: Target Sequence

<400> SEQUENCE: 158
gagtttgcac tgaggatga                                               19

<210> SEQ ID NO 159
<211> LENGTH: 19
<212> TYPE: DNA
<213> ORGANISM: Artificial
<220> FEATURE:
<223> OTHER INFORMATION: Target Sequence

<400> SEQUENCE: 159
aaatggcgac aagaagatt                                               19

<210> SEQ ID NO 160
<211> LENGTH: 19
<212> TYPE: DNA
<213> ORGANISM: Artificial
<220> FEATURE:
```

```
<223> OTHER INFORMATION: Target Sequence

<400> SEQUENCE: 160
caaggtgaag agccagtac                                                    19

<210> SEQ ID NO 161
<211> LENGTH: 19
<212> TYPE: DNA
<213> ORGANISM: Artificial
<220> FEATURE:
<223> OTHER INFORMATION: Target Sequence

<400> SEQUENCE: 161
acttgctgac ggccatcca                                                    19

<210> SEQ ID NO 162
<211> LENGTH: 19
<212> TYPE: DNA
<213> ORGANISM: Artificial
<220> FEATURE:
<223> OTHER INFORMATION: Target Sequence

<400> SEQUENCE: 162
gctgatctat gcctttcaa                                                    19

<210> SEQ ID NO 163
<211> LENGTH: 19
<212> TYPE: DNA
<213> ORGANISM: Artificial
<220> FEATURE:
<223> OTHER INFORMATION: Target Sequence

<400> SEQUENCE: 163
gatctatgcc tttcaacta                                                    19

<210> SEQ ID NO 164
<211> LENGTH: 19
<212> TYPE: DNA
<213> ORGANISM: Artificial
<220> FEATURE:
<223> OTHER INFORMATION: Target Sequence

<400> SEQUENCE: 164
ctatgccttt caactagaa                                                    19

<210> SEQ ID NO 165
<211> LENGTH: 19
<212> TYPE: DNA
<213> ORGANISM: Artificial
<220> FEATURE:
<223> OTHER INFORMATION: Target Sequence

<400> SEQUENCE: 165
cataccacac ttacaatta                                                    19

<210> SEQ ID NO 166
<211> LENGTH: 19
<212> TYPE: DNA
<213> ORGANISM: Artificial
<220> FEATURE:
<223> OTHER INFORMATION: Target Sequence

<400> SEQUENCE: 166
tccgtgtgat tgtctttga                                                    19
```

```
<210> SEQ ID NO 167
<211> LENGTH: 19
<212> TYPE: DNA
<213> ORGANISM: Artificial
<220> FEATURE:
<223> OTHER INFORMATION: Target Sequence

<400> SEQUENCE: 167
ccgtgtgatt gtctttgaa                                                 19

<210> SEQ ID NO 168
<211> LENGTH: 19
<212> TYPE: DNA
<213> ORGANISM: Artificial
<220> FEATURE:
<223> OTHER INFORMATION: Target Sequence

<400> SEQUENCE: 168
ttagaacagt ccagcaaat                                                 19

<210> SEQ ID NO 169
<211> LENGTH: 19
<212> TYPE: DNA
<213> ORGANISM: Artificial
<220> FEATURE:
<223> OTHER INFORMATION: Target Sequence

<400> SEQUENCE: 169
tgaaaggtgt gctagaaca                                                 19

<210> SEQ ID NO 170
<211> LENGTH: 19
<212> TYPE: DNA
<213> ORGANISM: Artificial
<220> FEATURE:
<223> OTHER INFORMATION: Target Sequence

<400> SEQUENCE: 170
gaaaggtgtg ctagaacaa                                                 19

<210> SEQ ID NO 171
<211> LENGTH: 19
<212> TYPE: DNA
<213> ORGANISM: Artificial
<220> FEATURE:
<223> OTHER INFORMATION: Target Sequence

<400> SEQUENCE: 171
ttgattgcct atggatcaa                                                 19

<210> SEQ ID NO 172
<211> LENGTH: 19
<212> TYPE: DNA
<213> ORGANISM: Artificial
<220> FEATURE:
<223> OTHER INFORMATION: Target Sequence

<400> SEQUENCE: 172
ccagcgagag agtttcaaa                                                 19

<210> SEQ ID NO 173
<211> LENGTH: 19
<212> TYPE: DNA
<213> ORGANISM: Artificial
<220> FEATURE:
<223> OTHER INFORMATION: Target Sequence
```

```
<400> SEQUENCE: 173
atgtttaatc agcgatgta                                                  19

<210> SEQ ID NO 174
<211> LENGTH: 19
<212> TYPE: DNA
<213> ORGANISM: Artificial
<220> FEATURE:
<223> OTHER INFORMATION: Target Sequence

<400> SEQUENCE: 174
gtttaatcag cgatgtata                                                  19

<210> SEQ ID NO 175
<211> LENGTH: 19
<212> TYPE: DNA
<213> ORGANISM: Artificial
<220> FEATURE:
<223> OTHER INFORMATION: Target Sequence

<400> SEQUENCE: 175
ccaaagccgg attcttaat                                                  19

<210> SEQ ID NO 176
<211> LENGTH: 19
<212> TYPE: DNA
<213> ORGANISM: Artificial
<220> FEATURE:
<223> OTHER INFORMATION: Target Sequence

<400> SEQUENCE: 176
ccggagagtt atcctgata                                                  19

<210> SEQ ID NO 177
<211> LENGTH: 19
<212> TYPE: DNA
<213> ORGANISM: Artificial
<220> FEATURE:
<223> OTHER INFORMATION: Target Sequence

<400> SEQUENCE: 177
cggagagtta tcctgataa                                                  19

<210> SEQ ID NO 178
<211> LENGTH: 19
<212> TYPE: DNA
<213> ORGANISM: Artificial
<220> FEATURE:
<223> OTHER INFORMATION: Target Sequence

<400> SEQUENCE: 178
ggagagttat cctgataaa                                                  19

<210> SEQ ID NO 179
<211> LENGTH: 19
<212> TYPE: DNA
<213> ORGANISM: Artificial
<220> FEATURE:
<223> OTHER INFORMATION: Target Sequence

<400> SEQUENCE: 179
gagagttatc ctgataaat                                                  19

<210> SEQ ID NO 180
<211> LENGTH: 19
```

```
<212> TYPE: DNA
<213> ORGANISM: Artificial
<220> FEATURE:
<223> OTHER INFORMATION: Target Sequence

<400> SEQUENCE: 180
ggttctctct gacctttca                                              19

<210> SEQ ID NO 181
<211> LENGTH: 19
<212> TYPE: DNA
<213> ORGANISM: Artificial
<220> FEATURE:
<223> OTHER INFORMATION: Target Sequence

<400> SEQUENCE: 181
tctgaccttt catcgtaaa                                              19

<210> SEQ ID NO 182
<211> LENGTH: 19
<212> TYPE: DNA
<213> ORGANISM: Artificial
<220> FEATURE:
<223> OTHER INFORMATION: Target Sequence

<400> SEQUENCE: 182
ctacttctct gttgtcaaa                                              19

<210> SEQ ID NO 183
<211> LENGTH: 19
<212> TYPE: DNA
<213> ORGANISM: Artificial
<220> FEATURE:
<223> OTHER INFORMATION: Target Sequence

<400> SEQUENCE: 183
ggtcttagtt ctggttgat                                              19

<210> SEQ ID NO 184
<211> LENGTH: 19
<212> TYPE: DNA
<213> ORGANISM: Artificial
<220> FEATURE:
<223> OTHER INFORMATION: Target Sequence

<400> SEQUENCE: 184
taccacagaa tacggaaga                                              19

<210> SEQ ID NO 185
<211> LENGTH: 19
<212> TYPE: DNA
<213> ORGANISM: Artificial
<220> FEATURE:
<223> OTHER INFORMATION: Target Sequence

<400> SEQUENCE: 185
cactatcacg agcctttgt                                              19

<210> SEQ ID NO 186
<211> LENGTH: 19
<212> TYPE: DNA
<213> ORGANISM: Artificial
<220> FEATURE:
<223> OTHER INFORMATION: Target Sequence

<400> SEQUENCE: 186
```

-continued ccacaaagta tctaacaaa                                                    19

<210> SEQ ID NO 187
<211> LENGTH: 19
<212> TYPE: DNA
<213> ORGANISM: Artificial
<220> FEATURE:
<223> OTHER INFORMATION: Target Sequence

<400> SEQUENCE: 187
aaaccaatgt gcagactga                                                    19

<210> SEQ ID NO 188
<211> LENGTH: 19
<212> TYPE: DNA
<213> ORGANISM: Artificial
<220> FEATURE:
<223> OTHER INFORMATION: Target Sequence

<400> SEQUENCE: 188
ttggcagaac tcagttaaa                                                    19

<210> SEQ ID NO 189
<211> LENGTH: 19
<212> TYPE: DNA
<213> ORGANISM: Artificial
<220> FEATURE:
<223> OTHER INFORMATION: Target Sequence

<400> SEQUENCE: 189
ataacatact ggccgttct                                                    19

<210> SEQ ID NO 190
<211> LENGTH: 19
<212> TYPE: DNA
<213> ORGANISM: Artificial
<220> FEATURE:
<223> OTHER INFORMATION: Target Sequence

<400> SEQUENCE: 190
atcctaagtc tcttacaaa                                                    19

<210> SEQ ID NO 191
<211> LENGTH: 4465
<212> TYPE: DNA
<213> ORGANISM: Homo sapiens

<400> SEQUENCE: 191
cctgcagcct ccggagtcag tgccgcgcgc ccgccgcccc gcgccttcct gctcgccgca        60
cctccgggag ccggggcgca cccagcccgc agcgccgcct cccgccccgc gccgcctccg       120
accgcaggcc gagggccgcc actggccggg gggaccgggc agcagcttgc ggccgcggag       180
ccgggcaacg ctggggactg cgccttttgt ccccggaggt ccctggaagt ttgcggcagg       240
acgcgcgcgg ggaggcggcg gaggcagccc cgacgtcgcg gagaacaggg cgcagagccg       300
gcatgggcat cgggcgcagc gagggggggcc ggcgcggggc agccctgggc gtgctgctgg       360
cgctgggcgc ggcgcttctg gccgtgggct cggccagcga gtacgactac gtgagcttcc       420
agtcggacat cggcccgtac cagagcgggc gcttctacac caagccacct cagtgcgtgg       480
acatccccgc ggacctgcgg ctgtgccaca acgtgggcta caagaagatg gtgctgccca       540
acctgctgga gcacgagacc atggcggagg tgaagcagca ggccagcagc tgggtgcccc       600
tgctcaacaa gaactgccac gccggcaccc aggtcttcct ctgctcgctc ttcgcgcccg       660

```
tctgcctgga ccggcccatc tacccgtgtc gctggctctg cgaggccgtg cgcgactcgt    720
gcgagccggt catgcagttc ttcggcttct actgggccga gatgcttaag tgtgacaagt    780
tccccgaggg ggacgtctgc atcgccatga cgccgcccaa tgccaccgaa gcctccaagc    840
cccaaggcac aacggtgtgt cctccctgtg acaacgagtt gaaatctgag gccatcattg    900
aacatctctg tgccagcgag tttgcactga ggatgaaaat aaaagaagtg aaaaagaaa     960 atggcgacaa gaagattgtc cccaagaaga agaagcccct gaagttgggg cccatcaaga   1020
agaaggacct gaagaagctt gtgctgtacc tgaagaatgg ggctgactgt ccctgccacc   1080
agctggacaa cctcagccac cacttcctca tcatgggccg caaggtgaag agccagtact   1140
tgctgacggc catccacaag tgggacaaga aaacaaggga gttcaaaaac ttcatgaaga   1200
aaatgaaaaa ccatgagtgc cccacctttc agtccgtgtt taagtgattc cccgggggc    1260 agggtgggga gggagcctcg ggtgggggtgg gagcgggggg gacagtgccc cgggaacccg   1320
gtgggtcaca cacgcacact gcgcctgtca gtagtggaca ttgtaatcca gtcggcttgt   1380
tcttgcagca ttcccgctcc cttccctcca tagccacgct ccaaacccca gggtagccat   1440
ggccgggtaa agcaagggcc atttagatta ggaaggtttt taagatccgc aatgtggagc   1500
agcagccact gcacaggagg aggtgacaaa ccatttccaa cagcaacaca gccactaaaa   1560
cacaaaaagg gggattgggc ggaaagtgag agccagcagc aaaaactaca ttttgcaact   1620
tgttggtgtg gatctattgg ctgatctatg cctttcaact agaaaattct aatgattggc   1680
aagtcacgtt gttttcaggt ccagagtagt ttctttctgt ctgctttaaa tggaaacaga   1740
ctcataccac acttacaatt aaggtcaagc ccagaaagtg ataagtgcag ggaggaaaag   1800
tgcaagtcca ttatgtaata gtgacagcaa agggaccagg ggagaggcat tgccttctct   1860
gcccacagtc tttccgtgtg attgtctttg aatctgaatc agccagtctc agatgcccca   1920
aagtttcggt tcctatgagc ccggggcatg atctgatccc caagacatgt ggaggggcag   1980
cctgtgcctg cctttgtgtc agaaaaagga aaccacagtg agcctgagag agacggcgat   2040
tttcgggctg agaaggcagt agtttttcaaa acacatagtt aaaaaagaaa caaatgaaaa   2100
aaattttaga acagtccagc aaattgctag tcagggtgaa ttgtgaaatt gggtgaagag   2160
cttaggattc taatctcatg ttttttccctt ttcacatttt taaaagaaca atgacaaaca   2220
cccacttatt tttcaaggtt ttaaaacagt ctacattgag catttgaaag gtgtgctaga   2280
acaaggtctc ctgatccgtc cgaggctgct tcccagagga gcagctctcc ccaggcattt   2340
gccaagggag gcggatttcc ctggtagtgt agctgtgtgg cttttccttcc tgaagagtcc   2400 gtggttgccc tagaacctaa cacccccctag caaaactcac agagctttcc gttttttttct   2460 ttcctgtaaa gaaacatttc ctttgaactt gattgcctat ggatcaaaga aattcagaac   2520
agcctgcctg tcccccgca cttttttacat atatttgttt catttctgca gatggaaagt   2580
tgacatgggt ggggtgtccc catccagcga gagagtttca aaagcaaaac atctctgcag   2640 ttttttcccaa gtaccctgag atacttccca aagcccttat gtttaatcag cgatgtatat   2700
aagccagttc acttagacaa ctttaccctt cttgtccaat gtacaggaag tagttctaaa   2760
aaaaatgcat attaatttct tcccccaaag ccggattctt aattctctgc aacactttga   2820
ggacatttat gattgtccct ctgggccaat gcttataccc agtgaggatg ctgcagtgag   2880
gctgtaaagt ggcccctgc ggccctagcc tgacccggag gaaaggatgg tagattctgt   2940
taactcttga agactccagt atgaaaatca gcatgcccgc ctagttacct accggagagt   3000
```

| | |
|---|---|
| tatcctgata aattaacctc tcacagttag tgatcctgtc cttttaacac ctttttttgtg | 3060 |
| gggttctctc tgacctttca tcgtaaagtg ctggggacct taagtgattt gcctgtaatt | 3120 |
| ttggatgatt aaaaaatgtg tatatatatt agctaattag aaatattcta cttctctgtt | 3180 |
| gtcaaactga aattcagagc aagttcctga gtgcgtggat ctgggtctta gttctggttg | 3240 |
| attcactcaa gagttcagtg ctcatacgta tctgctcatt ttgacaaagt gcctcatgca | 3300 |
| accgggccct ctctctgcgg cagagtcctt agtggagggg tttacctgga acattagtag | 3360 |
| ttaccacaga atacggaaga gcaggtgact gtgctgtgca gctctctaaa tgggaattct | 3420 |
| caggtaggaa gcaacagctt cagaaagagc tcaaaataaa ttggaaatgt gaatcgcagc | 3480 |
| tgtgggtttt accaccgtct gtctcagagt cccaggacct tgagtgtcat tagttacttt | 3540 |
| attgaaggtt ttagacccat agcagctttg tctctgtcac atcagcaatt tcagaaccaa | 3600 |
| aagggaggct ctctgtaggc acagagctgc actatcacga gcctttgttt ttctccacaa | 3660 |
| agtatctaac aaaaccaatg tgcagactga ttggcctggt cattggtctc cgagagagga | 3720 |
| ggtttgcctg tgatttccta attatcgcta gggccaaggt gggatttgta aagctttaca | 3780 |
| ataatcattc tggatagagt cctgggaggt ccttggcaga actcagttaa atctttgaag | 3840 |
| aatatttgta gttatcttag aagatagcat gggaggtgag gattccaaaa acattttatt | 3900 |
| tttaaaatat cctgtgtaac acttggctct tggtacctgt gggttagcat caagttctcc | 3960 |
| ccagggtaga attcaatcag agctccagtt tgcatttgga tgtgtaaatt acagtaatcc | 4020 |
| catttcccaa acctaaaatc tgttttttctc atcagactct gagtaactgg ttgctgtgtc | 4080 |
| ataacttcat agatgcagga ggctcaggtg atctgtttga ggagagcacc ctaggcagcc | 4140 |
| tgcagggaat aacatactgg ccgttctgac ctgttgccag cagatacaca ggacatggat | 4200 |
| gaaattcccg tttcctctag tttcttcctg tagtactcct ctttttagatc ctaagtctct | 4260 |
| tacaaaagct ttgaatactg tgaaaatgtt ttacattcca tttcatttgt gttgtttttt | 4320 |
| taactgcatt ttaccagatg ttttgatgtt atcgcttatg ttaatagtaa ttcccgtacg | 4380 |
| tgttcatttt attttcatgc ttttttcagcc atgtatcaat attcacttga ctaaaatcac | 4440 |
| tcaattaatc aatgaaaaaa aaaaa | 4465 |

<210> SEQ ID NO 192
<211> LENGTH: 19
<212> TYPE: DNA
<213> ORGANISM: Artificial
<220> FEATURE:
<223> OTHER INFORMATION: Target Sequence

<400> SEQUENCE: 192
cattagtagt taccacaga        19

<210> SEQ ID NO 193
<211> LENGTH: 19
<212> TYPE: RNA
<213> ORGANISM: Artificial
<220> FEATURE:
<223> OTHER INFORMATION: Sense Strand

<400> SEQUENCE: 193
cgugggcuac aagaagaug        19

<210> SEQ ID NO 194
<211> LENGTH: 19
<212> TYPE: RNA
<213> ORGANISM: Artificial

```
<220> FEATURE:
<223> OTHER INFORMATION: Antisense Strand

<400> SEQUENCE: 194
caucuucuug uagcccacg                                                        19

<210> SEQ ID NO 195
<211> LENGTH: 25
<212> TYPE: DNA
<213> ORGANISM: Artificial
<220> FEATURE:
<223> OTHER INFORMATION: Sense Strand

<400> SEQUENCE: 195
cgtgggctac aagaagatgg tgctg                                                 25

<210> SEQ ID NO 196
<211> LENGTH: 25
<212> TYPE: RNA
<213> ORGANISM: Artificial
<220> FEATURE:
<223> OTHER INFORMATION: Sense Strand

<400> SEQUENCE: 196
cgugggcuac aagaagaugg ugcug                                                 25

<210> SEQ ID NO 197
<211> LENGTH: 27
<212> TYPE: RNA
<213> ORGANISM: Artificial
<220> FEATURE:
<223> OTHER INFORMATION: Antisense Strand

<400> SEQUENCE: 197
cagcaccauc uucuuguagc ccacguu                                               27
```